US011796617B2

(12) United States Patent
Wang et al.

(10) Patent No.: US 11,796,617 B2
(45) Date of Patent: Oct. 24, 2023

(54) SYSTEM AND METHOD FOR RECONSTRUCTION OF MAGNETIC RESONANCE IMAGES ACQUIRED WITH PARTIAL FOURIER ACQUISITION

(71) Applicants: University of Cincinnati, Cincinnati, OH (US); Children's Hospital Medical Center, Cincinnati, OH (US)

(72) Inventors: Jinghua Wang, Mason, OH (US); Lili He, Mason, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 169 days.

(21) Appl. No.: 17/420,246

(22) PCT Filed: Apr. 9, 2019

(86) PCT No.: PCT/US2019/026449
§ 371 (c)(1),
(2) Date: Jul. 1, 2021

(87) PCT Pub. No.: WO2020/142109
PCT Pub. Date: Jul. 9, 2020

(65) Prior Publication Data
US 2022/0065967 A1 Mar. 3, 2022

Related U.S. Application Data

(60) Provisional application No. 62/788,258, filed on Jan. 4, 2019.

(51) Int. Cl.
*G01V 3/00* (2006.01)
*G01R 33/561* (2006.01)
(Continued)

(52) U.S. Cl.
CPC .......... *G01R 33/5611* (2013.01); *A61B 5/055* (2013.01); *G01R 33/4818* (2013.01); *G01R 33/56509* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 5,245,282 A 9/1993 Mugler et al.
6,242,916 B1 6/2001 King
(Continued)

FOREIGN PATENT DOCUMENTS

CN 103654789 A * 3/2014 ............. G01R 33/50
CN 104248437 B * 4/2017
(Continued)

OTHER PUBLICATIONS

MRI_Ariticle.pdf downloaded from Internet on Feb. 4, 2023. (Year: 2023).*
(Continued)

*Primary Examiner* — Walter L Lindsay, Jr.
*Assistant Examiner* — Frederick Wenderothy
(74) *Attorney, Agent, or Firm* — DINSMORE & SHOHL LLP

(57) ABSTRACT

A method for k-space registration is provided. The method of k-space registration includes receiving a first partial k-space dataset for an object and a second partial k-space dataset for the object, selecting the first partial k-space dataset as a reference, selecting feature for estimating a transformation matrix for transforming k-space data, estimating a transformation matrix based on the feature of entire or part of the first partial k-space dataset and the feature of the second partial k-space dataset corresponding to the entire
(Continued)

or part of the first partial k-space dataset, correcting the second partial k-space dataset based on the transformation matrix, and obtaining the corrected second partial k-space dataset. The present method is further used for partial Fourier reconstruction.

20 Claims, 16 Drawing Sheets

(51) Int. Cl.
*A61B 5/055* (2006.01)
*G01R 33/48* (2006.01)
*G01R 33/565* (2006.01)

(58) Field of Classification Search
USPC .......................................... 324/309
See application file for complete search history.

(56) References Cited

U.S. PATENT DOCUMENTS

| | | | |
|---|---|---|---|
| 6,975,113 B1 | 12/2005 | Gurr | |
| 7,592,808 B1* | 9/2009 | King | G01R 33/56545 |
| | | | 324/307 |
| 9,658,304 B2* | 5/2017 | Lin | G01R 33/4818 |
| 2008/0240533 A1* | 10/2008 | Piron | G06T 5/50 |
| | | | 382/131 |
| 2011/0105884 A1 | 5/2011 | Beck | |
| 2014/0035579 A1* | 2/2014 | Paul | G01R 33/561 |
| | | | 324/309 |
| 2015/0071514 A1 | 3/2015 | Wang et al. | |
| 2016/0274209 A1* | 9/2016 | Dannels | G01R 33/4824 |
| 2017/0178318 A1 | 6/2017 | Wang et al. | |
| 2017/0287133 A1* | 10/2017 | Esparza Manzano | G06T 5/002 |
| 2018/0210055 A1* | 7/2018 | Ding | G01R 23/16 |
| 2018/0292498 A1 | 10/2018 | Shu et al. | |

FOREIGN PATENT DOCUMENTS

| | | | | |
|---|---|---|---|---|
| CN | 104217448 B | * | 11/2017 | |
| GB | 2325835 A | * | 12/1998 | G06T 15/08 |
| WO | WO-2017195666 A1 | * | 11/2017 | H04N 19/18 |

OTHER PUBLICATIONS

International Search Report dated Aug. 27, 2019, in reference to co-pending PCT/US2019/26449 filed Apr. 9, 2019.
Extended European Search Report dated Aug. 3, 2022 pertaining to EP application No. 19907102.8 filed Jul. 5, 2021, pp. 1-13.
Huang, F. et al. "Partial Fourier Reconstruction Through Data Fitting and Convolution in k-Space" Magnetic Resonance in Medicine, 2009, pp. 1261-1269, vol. 62.
McGibney, G. et al. "Quantitative Evaluation of Several Partial Fourier Reconstruction Algorithms Used in MRI" Magnetic Resonance in Medicine, 1993, pp. 51-59, vol. 30.
Bashir, S. et al. "Analysis of Partial K-Space Reconstruction Algorithms for Magnetic Resonance Imaging" 2014 International Conference on Issues and Challenges in Intelligent Computing Techniques (ICICT), 2014, pp. 736-742.

* cited by examiner

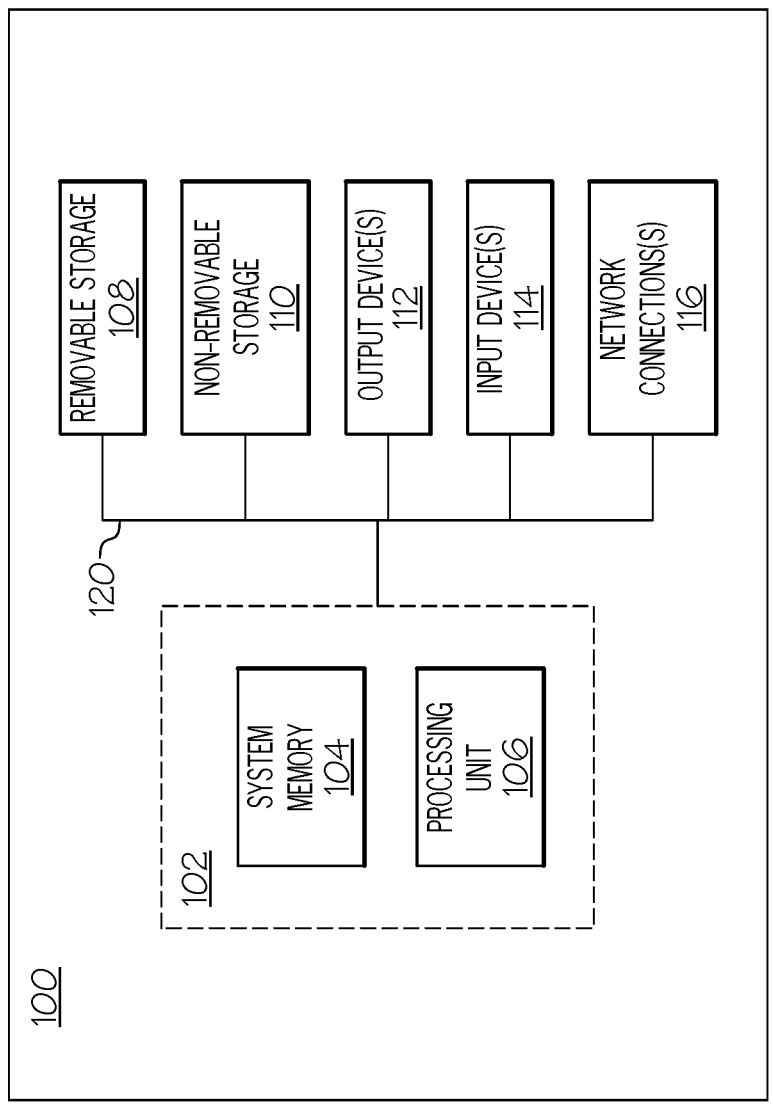

SYSTEM AND METHOD FOR RECONSTRUCTION OF MAGNETIC RESONANCE IMAGES ACQUIRED WITH PARTIAL FOURIER ACQUISITION

CROSS-REFERENCE TO RELATED APPLICATION

This application is a National Stage Entry under 35 U.S.C. § 371 of International Patent Application No. PCT/US2019/026449, filed Apr. 9, 2019, which claims priority to U.S. Provisional Application No. 62/788,258 filed on Jan. 4, 2019, the entire contents of which are herein incorporated by reference.

BACKGROUND

Technical Field

The present disclosure relates to methods and systems for the reconstruction of magnetic resonance image acquired with partial Fourier acquisition.

Description of the Related Art

Magnetic Resonance Imaging (MRI) is one of the most important modern medical imaging modalities. It has far less risk of side effects than most other imaging modalities such as radioscopy with x-rays or computed tomography because patients and medical personnel are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnosis of various diseases, such as tumors, strokes, heart problems, and spine diseases. A high-quality scan is important for maximizing diagnostic sensitivity and accuracy. Generally, high quality images are characterized by high signal to noise ratio (SNR), high contrast between normal and pathological tissues, low levels of artifacts, and appropriate spatial-temporal resolution In order to obtain a detectable MR signal, the object/subject examined is positioned in a homogeneous static magnetic field so that the object's nuclear spins generate net magnetization oriented along the static magnetic field. The net magnetization is rotated away from the static magnetic field using a radio frequency (RF) excitation field with the same frequency as the Larmor frequency of the nucleus. The angle of rotation is determined by the field strength of the RF excitation pulse and its duration. In the end of the RF excitation pulse, the nuclei, in relaxing to their normal spin conditions, generate a decaying signal (the "MR signal") at the same radio frequency as the RF excitation. The MR signal is picked up by a receive coil, amplified and processed. The acquired measurements, which are collected in the spatial frequency domain, are digitized and stored as complex numerical values in a "k-space" matrix. An associated MR image can be reconstructed from the k-space data, for example, by an inverse 2D or 3D fast Fourier transformation (FFT) from the raw k-space data.

Most MRI scans will take many minutes to acquire the data with reasonable image quality. The reduced scan time increases patient throughput, improves patient comfort, and improves image quality by reducing motion artifacts. The reduction of scan time is very important for MRI scans, particularly in cardiac MR imaging and pediatric imaging. Fast MRI acquisition techniques, such as partial Fourier, compressed sense, simultaneous multislice and parallel imaging, have been widely used for reducing the MRI scan time over the past decades. Among them, partial Fourier has been a popular MRI acquisition technique where the amount of k-space samples are reduced, that is only part of k-space are acquired. Several reconstruction methods have been developed to recover the full k-space from the partial Fourier acquisition, such as Zero-filling, conjugate (or Hermitian) synthesis, the Margosian algorithm, homodyne and the projection-onto-convex-sets (POCS) algorithm. Most of these methods estimate a phase information from low-resolution image which is created from the center of partial Fourier k-space data.

U.S. Pat. No. 6,242,916 B1 to Kevin F. King discloses that the partial k-space data sets are filled with complex conjugate data according to Hermitian symmetry which are processed using a combination of the Homodyne reconstruction method and the Sense processing method.

U.S. Pat. No. 6,975,113 B1 to David H. Gurr discloses that the unacquired k-space data in partial Fourier acquisition is created according to either Hermitian symmetry or zero fill in both phase-encoding and frequency-encoding directions. And then, the unacquired k-space data are filled out by homodyne and POCS algorithm in image domain in order to reduce the difference between the reconstructed images and true images.

U.S. Patent Application Publication No. 2017/0178318A1 to Qiu Wang and Esther Raithel discloses that an iterative reconstruction process of partial Fourier k-space dataset is carried out with phase correction based on the phase corresponding to the low-resolution image which is created by a symmetrically sampled k-space center dataset from the partial Fourier k-space dataset.

U.S. Patent Application Publication No. 2018/0292498 to Yunhong Su et al. discloses a method to reconstruct image acquired with partial Fourier acquisition and an asymmetric 3D shells k-space trajectory. The acquired images are reconstructed by a non-iterative homodyne reconstruction based on Hermitian symmetry.

The reconstruction of images acquired with partial Fourier acquisition has been one of the oldest and the toughest MRI techniques. The patents and literatures mentioned above mainly focus on reconstructing MR image acquired with the partial Fourier k-space by Hermitian symmetry and phase information correction which is estimated using low resolution image which is created by the central k-space of partial Fourier k-space dataset. However, the low-resolution phase estimate in the image space is prone to error. Additionally, the phase estimation is only associated with the effect of translation motion on un-acquired high spatial frequency components because phase shift in image domain corresponds to a translation in k-space, allowing only the effect to be corrected. The effect of rotation motion on un-acquired high spatial frequency components is not appropriately corrected.

Image Registration in k-Space Domain is Disclosed in the Following References:

The paper "Retrospective Rigid Motion Correction in k-Space for Segmented Radial MRI" in IEEE Trans Med Imaging. 2014; 33:1-10 to Ghislain Vaillant et al. discloses a method for estimating a transformation matrix of rigid motion that is derived using the inherent correlation between radial segments in k-space. The method combines the self-navigation with the correlation of adjacent segments in k-space for measuring and correcting for rigid motion in radial trajectory k-space sampling.

The abstract "Registration of MR data in the k-space domain using projections" in Proc. ISMRM 11th Annual meeting, Toronto, Canada (2003) Page 929 to W. Scott Hoge and Carl☐Fredrik Westin reviews a method based on this Fourier shift theorem to estimate translational shifts between two images with subpixel resolution. They extend to identification of image rotations using a pseudo-basis set constructed of circular harmonic functions.

SUMMARY

Described herein is a method to reconstruct a magnetic Resonance (MR) image acquired with partial Fourier k-space dataset.

In one embodiment, the method includes receiving a first partial k-space dataset for an object and a second partial k-space dataset for the object; selecting the first partial k-space dataset as a reference; selecting feature for estimating a transformation matrix for transforming k-space data; estimating a transformation matrix based on the feature of entire or part of the first partial k-space dataset and the feature of the second partial k-space dataset corresponding to the entire or part of the first partial k-space dataset; correcting the second partial k-space dataset based on the transformation matrix; and obtaining the corrected second partial k-space dataset.

In another embodiment, the method includes acquiring a first partial k-space dataset for a target area using an MRI scanner, creating a second partial k-space dataset for the target area based on Hermitian symmetry of the first partial k-space dataset, calculating a transformation matrix based on the first partial k-space dataset and the second partial k-space dataset, correcting the second partial k-space dataset using the transformation matrix, obtaining a full k-space dataset for the target area based on at least one of the corrected second partial k-space dataset, the first partial k-space dataset, and a third k-space dataset; and constructing an image for the target area based on the full k-space dataset.

In another embodiment, a system to improve image quality and efficiency using optimal variable flip angles for a magnetic resonance imaging (MRI) protocol is provided. The system includes a magnetic field generating unit configured to apply a plurality of RF pulses with a variable flip angle to a target area in the object; a receiver configured to receive MR signals from the target area; a processing unit; a system memory; and machine readable instructions stored in the system memory. The processing unit is configured to: acquire a first partial k-space dataset for the target area based on the MR signals; create a second partial k-space dataset for the target area based on Hermitian symmetry of the first partial k-space dataset; calculate a transformation matrix based on the first partial k-space dataset and the second partial k-space dataset; correct the second partial k-space dataset using the transformation matrix; obtaining a full k-space dataset for the target area based on at least one of the corrected second partial k-space dataset, the first partial k-space dataset, and a third k-space dataset; and reconstruct an image for the target area based on the full k-space dataset Alternatively or additionally, the transformation matrix in k-space domain may be at least one of an affine transform matrix, a rigid transform matrix, a linear transform matrix, a non-linear transform matrix, but not limited to, and a non-rigid transform matrix.

Alternatively or additionally, the transformation matrix is used to correct translation and rotation motions of the entire or part of k-space dataset.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 1A is an example computing device.

DETAILED DESCRIPTION

Definition

Figure 1:
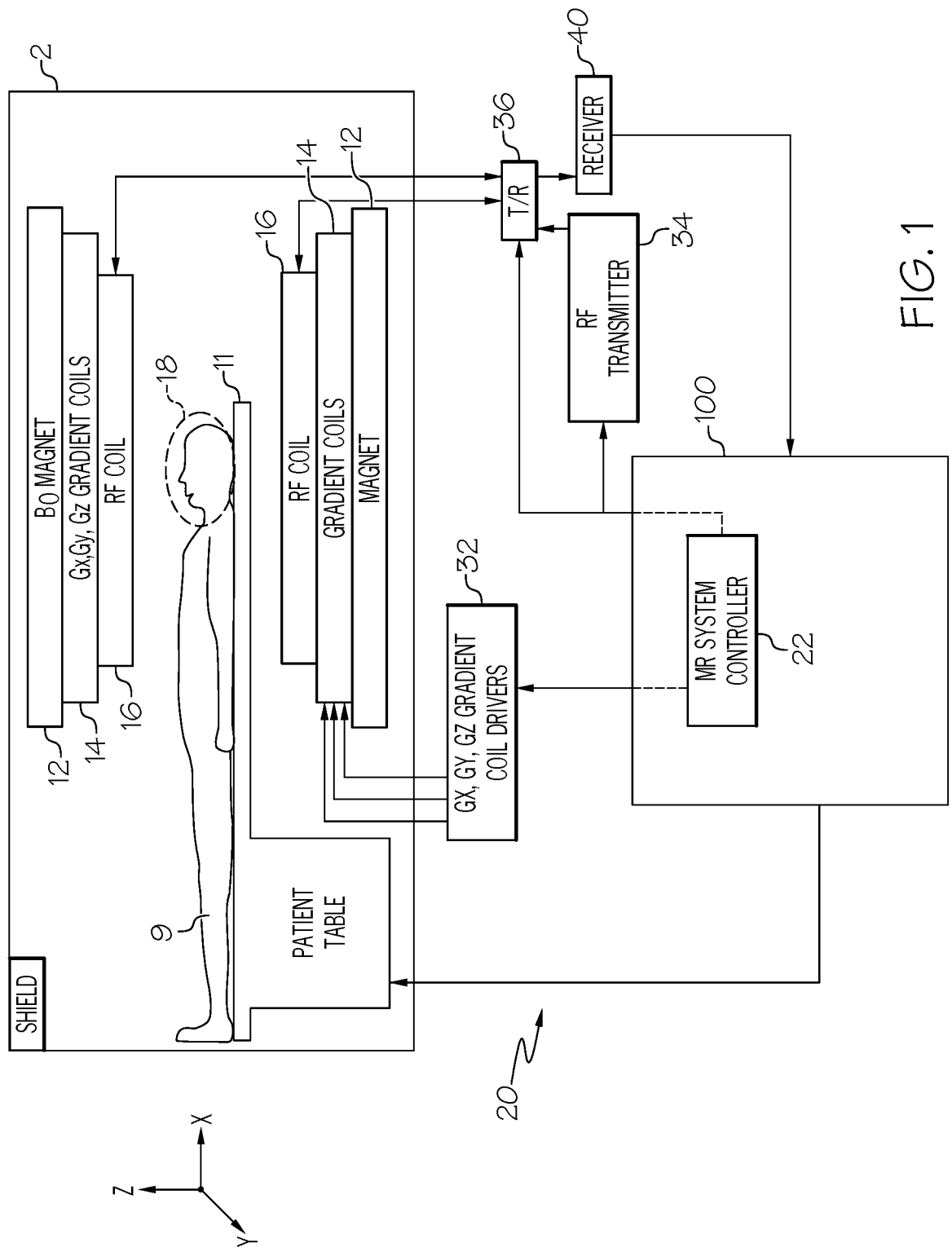
FIG. 1 is a diagram illustrating an example MRI system.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for optimizing MRI scanner settings (also referred to herein as "basic scanner settings"), MRI protocols, variable flip angle, k-space strategy, and/or imaging parameters with regard to MRI modalities, it will become evident to those skilled in the art that the implementations are not limited thereto, but are applicable to other image modalities such as, computed tomography, for example. Additionally, this disclosure contemplates that MRI modalities include MRI techniques with administration of contrast agents, for example, contrast enhanced MR angiography. This disclosure contemplates that the images obtained using the techniques described herein can be directly employed in at least one of diagnosing diseases, monitoring prognosis and therapeutic responses, conducting treatment plans, and improving quantification of MRI. For example, the techniques described herein can be used for the diagnoses of specific diseases such as the standardization of the MRI protocol in The Alzheimer's Disease Neuroimaging Initiative. Additionally, the techniques described herein are optionally applicable to a group of individuals in a similar pathophysiological situation.

The term "each acquisition" and variations thereof as used herein is used synonymously with the term "each k-space line" or "each phase-encoding" or "each readout radiofrequency pulse" or "each echo" or "each readout gradient pulse" and variations thereof and are open, non-limiting terms.

The term "k-space" and variations (such as frequency domain or raw data) thereof as used herein indicate the data space in which MRI raw data is acquired. The k-space represents the spatial frequency information in two or three dimensions of an object. The k-space is defined as a space covered by the phase and frequency encoding data. In contrast to this, the Fourier-transformed counterpart of the k-space is defined as an image space or image domain. The relationship between k-space data and image data is the Fourier transformation. Each data point in k-space represents a different superposition of the tissue signals. Every point in the raw data matrix contains part of the information for the complete image. A point in the raw data matrix does not correspond to a point in the image matrix. The high spatial frequency components provide information about the borders and contours of the image, the detail of the structures. The low spatial frequency components provide information on the general contrast of the image.

The term "k-space trajectory" and variations thereof as used herein indicate the path traced in k-space domain during MRI data collection. The k-space trajectory is used to illustrate the acquisition strategy. It has great influences on artifacts and the image reconstruction.

The term "the corresponding part" and variations thereof as used herein indicate multiple k-space dataset having in the same geometric characters (such as position and size) relative to whole k-space datasets.

The term "reconstructing image" and variations thereof as used herein indicate a process for transforming the acquired k-space data (e.g. raw data) into images.

The term "functional system" and variations thereof as used herein include, but are not limited to, hardware, software to perform a function and/or an action.

The term "transformation matrix" or "correction matrix" and their variations thereof as used herein indicate that geometrical transformation of the MR raw data refers to the movement caused by object motion, imperfect hardware (gradient, $B_0$ inhomogeneity), object properties (chemical shift, susceptibility effect), and so on. There are two different categories of transformations—rigid and non-rigid transformations. It includes the four main types of transformations: translation, rotation, dilation and reflection.

The term "conjugate (or Hermitian) symmetry" and variations thereof as used herein indicate a fundamental property of Fourier transformations that the conjugate symmetry of the raw data in k-space is diagonal in nature. It includes frequency-encoding and phase-encoding symmetry in MRI system.

The term "reconstruction" and variations thereof as used herein indicate a mathematical process that generates MRI images from incomplete raw data acquired at many different conditions to improve image quality and reduce the artefacts.

MRI System Overview

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals. The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

Example Computing Device

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented. Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1. Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by, the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

OVERVIEW

Registration in K-Space Domain

One major challenge of the MRI is the relatively long acquisition time in order to obtain high quality, diagnostically interpretable images. Unfortunately, the duration of the data acquisition is long enough—of the order of a few seconds—for organ motion such as cardiac motion, respiration, blood flow, peristalsis or restlessness to cause artifacts such as blurring and replication—commonly termed as ghosting—in the reconstructed image. Even without subject motion, the gradient imperfect, susceptibility and scanner drift will lead to k-space data variation and degrade the image quality. Currently, medical image registration is generally conducted in image domain. In image domain, each pixel or voxel of a uniform phantom has an equal contribution to image quality or signal intensity in ideal case. Registration between images or segmented k-space data is often conducted using a transformation matrix. The transformation matrix is obtained by measuring rigid transformations between images from their Fourier pairs from the registration of low-resolution images. However, the Fourier transformation of low-resolution images between k-space domain and image domain can introduce truncation artifacts and then influence the accuracy of the transformation matrix. Particularly, phase correlation between two images or two segmented k-space data is very sensitive to the truncation artifacts.

Compared with image domain, k-space domain have the following advantages. First, in k-space domain, the point at the central k-space data has more weighted to contribute for signal intensity. The point at the peripheral k-space data contribute to image or resolution in details. While each pixel or voxel of a uniform phantom has an equal contribution to image quality or signal intensity in ideal case in image domain. Second, raw data in MRI is k-space data. Image data is obtained from Fourier transformation of k-space data. The transformation between k-space domain and image domain may introduce truncation artifacts. Third, the transformation matrix is performed using the spatial frequency content in k-space domain. The method is robust in the presence of intensity variations between the two images caused by radiofrequency inhomogeneity and other factors. Fourth, most visible artifacts in image domains, such as motion and Nyquist ghost, associated with the central k-space data. That is, the central k-space have a great influence on most artifacts, excluding blurring.

Figure 2A:
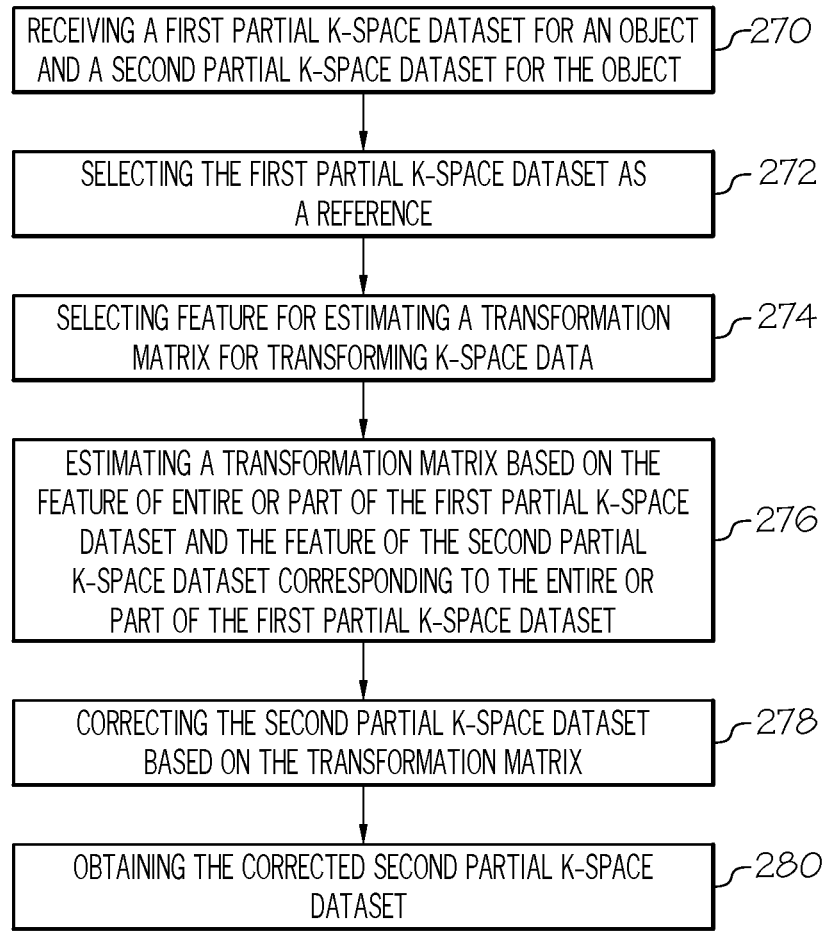
FIG. 2A depicts a flowchart for an example operation for reconstructing magnetic resonance image acquired with partial Fourier acquisition according to one example in the present disclosure.

FIG. 2A depicts a flowchart for an example operation for medical image registration in k-space domain according to one example in the present disclosure. In step 270, the computing device 100 receives a first partial k-space dataset for an object and a second partial k-space dataset for the object. In embodiments, the computing device 100 may acquire the first partial k-space dataset and the second partial k-space dataset from at least one modality including optical image, CT, MRI, ultrasound, and PET. In some embodiments, the computing device 100 may determine the first partial k-space dataset and the second partial k-space dataset from corresponding images of electronic storage on image domain. In some embodiments, the computing device 100 may determine the first partial k-space dataset and the second partial k-space dataset from a mathematic model.

In step 272, the computing device 100 selects the first partial k-space dataset as a reference. In step 274, the computing device 100 selects feature for estimating a transformation matrix for transforming k-space data. For example, the feature may include at least one of a phase of k-space data that object feature is mainly weighted by image magnitude, or a magnitude of k-space data that object feature is mainly weighted by image phase. As another example, the feature may include at least one of a phase of k-space data that are acquired with $T_1$-weighted or its variation sequence, or a magnitude of k-space data that are acquired with $T_2$-weighted, $T_2^*$-weighted, or their variation sequence.

In step 276, the computing device 100 estimates a transformation matrix based on the feature of entire or part of the first partial k-space dataset and the feature of the second partial k-space dataset corresponding to the entire or part of the first partial k-space dataset. The transformation matrix is configured to transform the first partial k-space dataset or the second partial k-space dataset by at least one of translation, rotation, scaling and shearing of the first partial k-space dataset, or the second partial k-space dataset. The transformation matrix may be calculated by magnitude-based k-space data registration of overlapping k-space data between the first partial k-space dataset and the second partial k-space dataset.

In step 278, the computing device 100 corrects the second partial k-space dataset based on the transformation matrix. For example, as discussed above in step 240 in FIG. 2A, the second partial k-space dataset is corrected based on the transformation matrix. In step 280, the corrected second partial k-space dataset is obtained.

The present disclosure estimates a transformation matrix in k-space directly. The present disclosure does not need a pseudo-basis set constructed of circular harmonic functions to estimate the transformation matrix of image rotations. The transformation matrix is directly estimated from magnitude of k-space data. Additionally, the present disclosure are available for not only translation and rotation, but also dilation and reflection.

First, the present disclosure focuses on the estimating un-acquired k-space data. Second, the present disclosure proposed for k-space registration for k-space lines in interframe. Third, the present disclosure uses at least one of magnitude, phase, complex, and their variation of k-space data as a feature for k-space registration. Finally, the present disclosure can be easily extend to any transform types of rigid and non-rigid transformations, including at least one of translation, rigid, affine transform types of for both phase and magnitude.

In embodiments, the feature includes at least one of a phase of k-space data that object feature is mainly weighted by image magnitude, or a magnitude of k-space data that object feature is mainly weighted by image phase.

In embodiments, the feature comprises at least one of a phase of k-space data that are acquired with $T_1$-weighted or its variation sequence, or a magnitude of k-space data that are acquired with $T_2$-weighted, $T_2^*$-weighted, or their variation sequence.

In embodiments, the transformation matrix is configured to transform the first partial k-space dataset or the second partial k-space dataset by at least one of translation, rotation, scaling and shearing of the first partial k-space dataset, or the second partial k-space dataset.

In embodiments, the modality is at least one of optical image, CT, MRI, ultrasound, and PET.

Partial Fourier Image Reconstruction

Partial Fourier imaging was first introduced in 1986 either to shorten image acquisition time by reducing the number of phase encoding or to shorten the echo time (TE) by reducing the number of frequency encoding. For example, with partial Fourier acquisition along phase-encoding direction, fast spin echo sequences, such as CUBE (GE Healthcare), SPACE (Sampling Perfection with Application optimized Contrasts by using different flip angle Evolutions; Siemens Healthcare) and VISTA (Volumetric ISotropic TSE Acquisition; Philips Healthcare), can acquire an image with whole-brain coverage within 6 minutes. Additionally, with partial Fourier imaging along frequency-encoding direction, echo planar imaging (EPI) based acquisition can achieve finer spatial resolution and higher b-value diffusion encoding in diffusion tensor imaging.

Partial Fourier acquisition only acquires a fraction (as little as one-half) of k-space data, and the remainder/missing of k-space data is synthesized (also referred as data fitting) to generate an entire MR image using an inverse Fourier transform. The most commonly used methods of synthesizing missing k-space data include zero filling and conjugate symmetry methods. Zero-filling method fills in the missing k-space data with zeros. Although zero-filling method has been widely applied by MRI manufactures in the commercial MRI scanners, it leads to truncation artifacts (e.g. blurring and Gibbs ringing artifacts) in the reconstructed image. Conjugate symmetry methods assume that the MRI image only comprises of real components and the missing of k-space data is synthesized by the complex conjugate of the acquired data based on the Hermitian symmetry property. Unfortunately, the Hermitian symmetry property is only valid when ignores the effects of eddy currents, non-uniform radiofrequency field, non-uniform BO, chemical shift, and motion gradient moments. Conjugate symmetry approximations are therefore not perfect. Conjugate symmetry data are proposed to be corrected through a phase variation along a phase-encoding direction by various methods, such as Margosian method, Homodyne detection method, and iterative Fourier correction algorithms. These methods work well for slow phase variation or short TE when the phase variation along frequency-encoding direction is ignorable. However, these methods are problematic for rapid phase variation and long TE acquisition, such as EPI acquisition for functional MRI and diffusion-weighted imaging. It is because the phase variation can change in both the phase-encoding and the frequency-encoding directions, though the partial Fourier acquisition is conducted only along the phase-encoding direction. Thus, the conjugate symmetry data should be corrected using multiple dimensional (n>2) transformation matrix.

Moreover, the phase information used by abovementioned methods was estimated in image domain via the Fourier transformation of central k-space data of both acquired data and conjugate symmetry data. Fourier transformation of the central k-space data between image domain and k-space domain (neglecting peripheral k-space data) can introduce truncation artifacts, especially with high partial Fourier accelerated factors. In order to avoid such truncation artifacts, the phase information were proposed to be approximately estimated in k-space domain through k-space convolution, which is similar to the calculation of convolution kernels in auto-calibration parallel imaging reconstruction. However, this method only focuses on the phase variation in the phase encode direction, but ignores the contribution of various factors on the phase variation in the frequency-encode direction.

Phase estimation plays an important role in conventional partial Fourier reconstruction techniques since incorrect phase estimation introduces errors and artifacts in the reconstructed images. Conventional partial Fourier techniques estimate phase over an image by low resolution image in image domain. Additionally, these techniques are one-dimensional or two-dimensional in nature. That is, the correction corrects for errors only along phase encoding direction. These techniques assume that the corrections are independent of frequency encoding direction. However, the failure of conjugate symmetry synthesized data are two dimensional or three dimensional in nature, and, therefore, a two-dimensional or three dimensional correction is required. That is, the correction should correct for errors along phase encoding directions and a frequency encoding direction. In the present disclosure, synthesized conjugate symmetry data is corrected using a multiple dimensional transformation matrix which is estimated using acquired central k-space data in k-space domain. The correction is based upon assumption that MRI environments (such as $B_0$ inhomogeneity, chemical shift, susceptibility effect, motion, and so on) introduce an identical displacement of k-space data for both acquired low frequency k-space components and un-acquired high frequency k-space component. That is, MRI environments have the same influences on acquired and un-acquired k-space data. As a result, a transform matrix may be estimated using acquired low-frequency k-space data and its Hermitian symmetry data. And then un-acquired high-frequency k-space data may be synthesized using estimated transform matrix and Hermitian symmetry data of acquired high-frequency k-space data.

Theory and Method

Figure 2B:
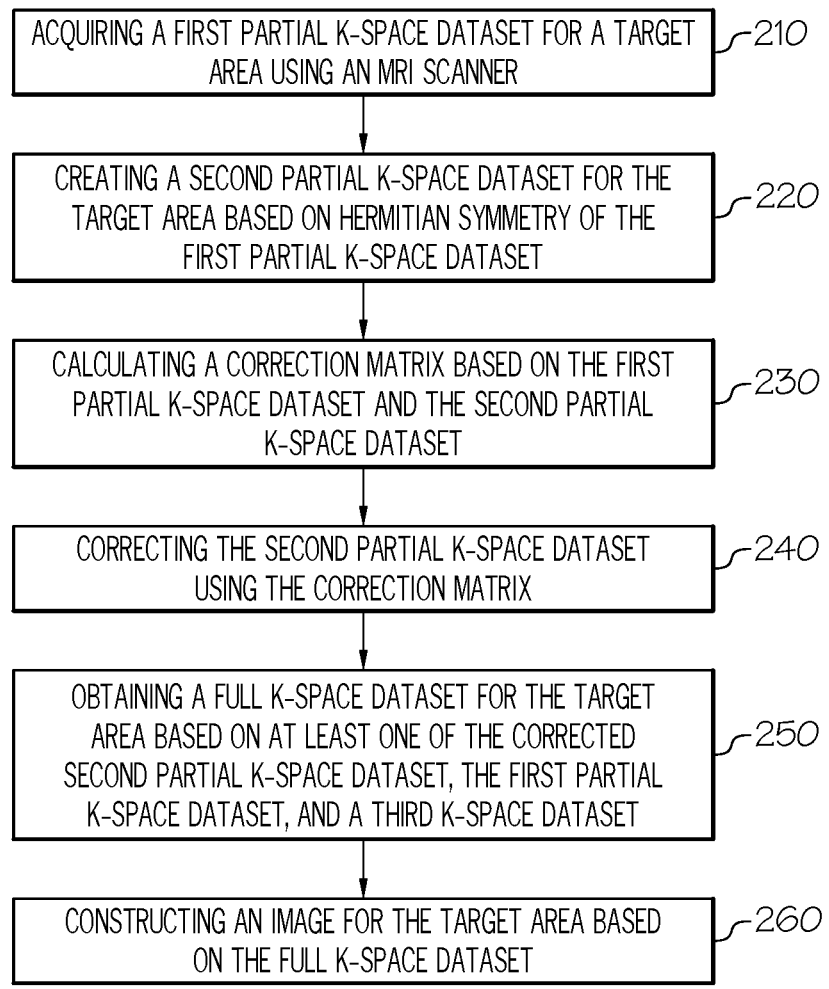
FIG. 2B depicts a flowchart for an example operation for reconstructing magnetic resonance image acquired with partial Fourier acquisition according to another example in the present disclosure.

FIG. 2B depicts a flowchart for an example operation for reconstructing magnetic resonance image acquired with partial Fourier acquisition according to one example in the present disclosure. In step 210, the computing device 100 acquires a first partial k-space dataset for a target area of an object using an MRI scanner. For example, as shown in FIG. 1, the computing device 100 receives MR signals from the transmitting and receiving unit 16 and acquires a first partial k-space dataset.

In embodiments, the first partial k-space dataset may be acquired in phase-encoding directions. In some embodiments, the first partial k-space dataset is acquired in frequency-encoding directions. In some embodiments, the first partial k-space dataset may be acquired using a combination of partial Fourier acquisition and other under-sampling techniques, such as compressed sensing and parallel imaging acquisitions.

In embodiments, the first partial k-space dataset may be acquired with at least one of $T_1$-weighted spin echo, $T_2$-weighted spin echo, fluid-attenuated inversion-recovery, $T_1$-weighted gradient-echo, $T_2^*$-weighted gradient echo, contrast enhanced $T_1$-weighted gradient echo, contrast enhanced $T_1$-weighted spin echo, diffusion-weighted spin echo, and their variations or combinations.

In embodiments, the first partial k-space dataset may be acquired with imaging sequence including, but not limited to, at least one of two spatial dimensional, three spatial dimensional, or three spatial dimensional plus temporal image acquisition. In some embodiments, the imaging sequence may include at least one of a gradient echo, echo planar or spin echo sequence with or without magnetization preparation, with or without under-sampling techniques, with or without parallel imaging techniques, or with or without Cartesian k-space trajectories In embodiments, the first partial k-space dataset may be acquired using k-space trajectory including at least one of rectilinear, echo planar, but not limited to, radial, Cartesian, non-Cartesian, Zig-Zag, stochastic, rosette, TWIRL, WHIRL and spiral trajectories. The first partial k-space dataset may be acquired according to a k-space sampling order including at least one of a sequential sampling order, a centric sampling order, an interleave sampling order, a reverse sampling order, a random sampling order, or a hybrid sampling order.

The target area may be at least a portion of a subject's body with or without disease. The portion of the subject's body may be at least one of an extremity, brain, spine, neck, chest, breast, joint, prostate, pelvis, or abdomen.

Figure 3A:
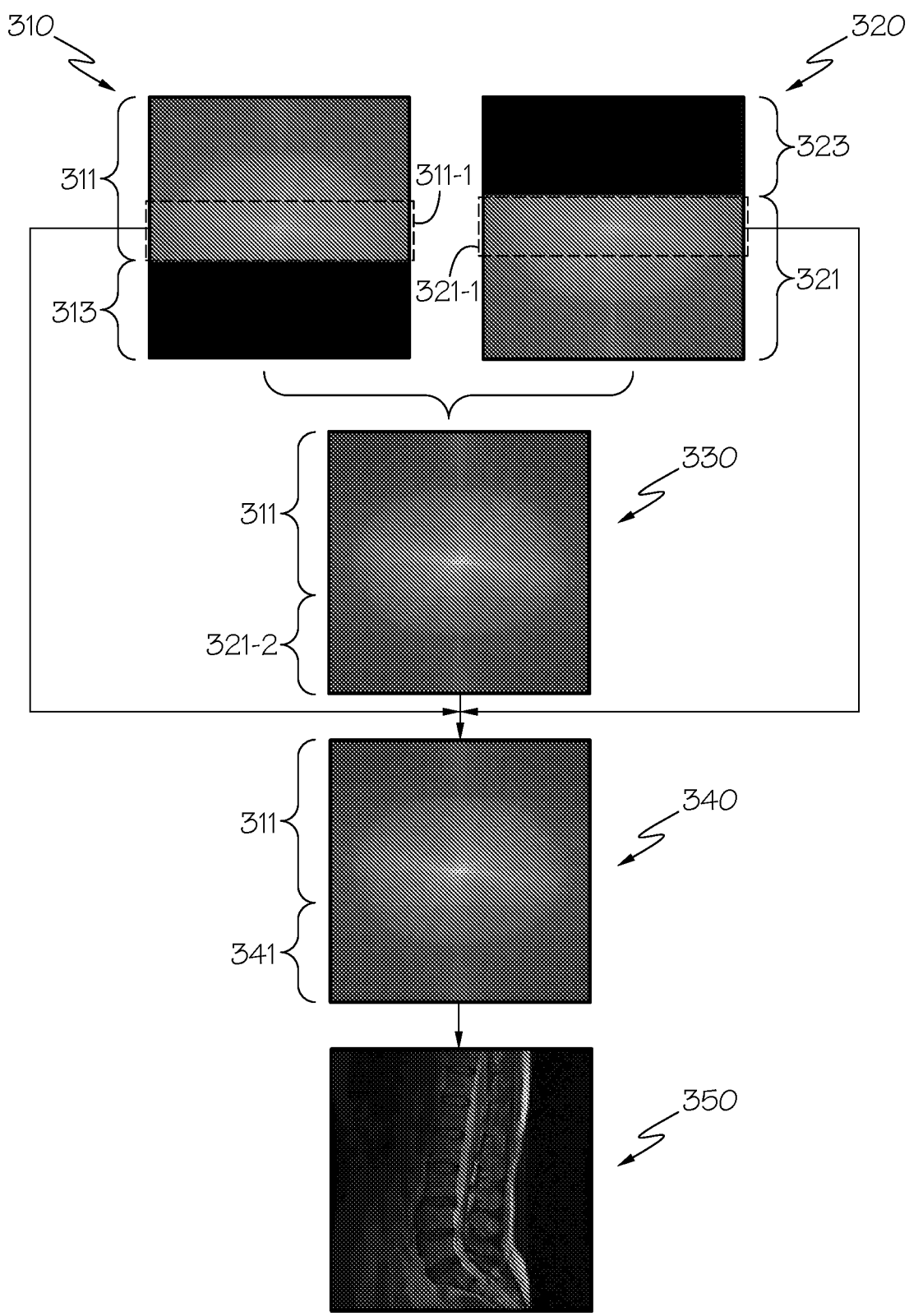
FIG. 3A is a flowchart illustrating a workflow for one-dimensional phase-encoding partial Fourier acquisition reconstruction according to one example in the present disclosure.

The first partial k-space data may be a partial Fourier k-space dataset, e.g., as shown in the partial Fourier k-space dataset 311 of the image 310 in FIG. 3A. Without loss of the generality, fully sampled 2D k-space data are to be set as $S(k_x, k_y)$, where $k_x$ and $k_y$ belongs to the full sampling range $[-k_{max}, k_{max}]$ As shown in the image 310, partial Fourier acquired data $S_{acquired}(k_x, k_y)$ ($k_x \in [-k_{max}, k_{max}]$ and $k_y \in [-k_N, k_{max}]$) are sampled only over the positive spatial frequencies plus a narrow band of low negative spatial frequencies along a phase encoding direction (y direction), where $k_N < k_{max}$.

The portion 313 in the image 310 represents portion where k-space data is not acquired by the MRI scanner. In embodiments, the MRI scanner may acquire the first partial k-space dataset with a fraction of less than 0.8. In some embodiments, the MRI scanner may acquire the first partial k-space dataset with a fraction of less than 0.6. In some embodiments, the MRI scanner may acquire the first partial k-space dataset with a fraction of less than 0.4. In step 220, the computing device 100 creates a second partial k-space dataset for the target area based on Hermitian symmetry of the first partial k-space dataset. Generally, magnetic resonance image signal without relaxation time effect may be described by:

$$s(\vec{k}) = \int p(\vec{r}) e^{-i\vec{k}\cdot\vec{r}} \cdot d\vec{r}^3 \qquad \text{Equation(1)}$$

Where k is the spatial frequency and $p(\vec{r})$ is nuclear spin density at the location of $\vec{r}$. The following Equation (2) is obtained according to Hermitian symmetry $$s(\vec{k}) = s^*(-\vec{k}) \qquad \text{Equation (2)}$$

Based on the Hermitian symmetry of the first partial k-space dataset as in Equation (2), the second partial k-space dataset for the target area is created. For example, the second partial k-space data may be created, as shown in the partial k-space data set 321 of the image 320 in FIG. 3A. Specifically, a part of the missing k-space data may be obtained by a synthesized $\hat{S}(k_x, k_y)$ using its complex conjugate as shown in Equation (3).

$$\hat{S}(k_x, k_y) = S^*_{acquired}(-k_x, -k_y) \qquad \text{Equation (3)}$$

where $k_x \in [-k_{max}, k_{max}]$ but $k_y \in [-k_{max}, k_N]$. The missing k-space data is $k_x \in [-k_{max}, k_{max}]$ but $k_y \in [-k_{max}, -(k_N+1)]$.

Since the assumption of Hermitian symmetry is not valid when the effects of eddy currents, non-uniform radiofrequency field, non-uniform $B_0$, chemical shift, and motion gradient moments are not ignored. Therefore, it is necessary to correct the synthesized data $\hat{S}(k_x, k_y)$. This issue may be addressed by introducing a transformation matrix that is described in step 230 below. The image 320 includes a portion 323 that is Hermitian Symmetry of the portion 313.

In step 230, the computing device 100 calculates a transformation matrix based on the first partial k-space dataset and the second partial k-space dataset. The transformation matrix may be used to correct the part of second partial k-space dataset for at least one of phase or rotation. The transformation matrix may be estimated from at least one of phase, magnitude, real, and imaginary of an acquired k-space dataset and Hermitian symmetry of the acquired k-space dataset. The transformation matrix in k-space domain may include, but not limited to, at least one of an affine transform matrix, a rigid transform matrix, a linear transform matrix, a non-linear transform, and a non-rigid transform matrix.

The transformation matrix is rigid and includes rotational matrix R and translational vector $\vec{T}$. The transformation matrix is estimated by the corresponding parts of $S_{acquired}(k_x, k_y)$ and $\hat{S}(k_x, k_y)$ using Equation (4) below:

$$\hat{S}(k_x, k_y) = S_{acquired}(R \cdot [k_x, k_y]) \cdot e^{-\pi i (R \cdot [k_x, k_y] \cdot \vec{T})} \qquad \text{Equation (4)}$$

where $k_x \in [-k_{max}, k_{max}]$ but $k_y \in [-k_N, k_N]$.

According to the Equation (4), it is noted that both R and $\vec{T}$ contribute to the phase image of k-space data. To simplify the reconstruction, correcting $S_{acquired}(k_x, k_y)$ using the transformation matrix of R is considered. The R may be estimated from the magnitude k-space data of the corresponding parts of $S_{acquired}(k_x, k_y)$ and $\hat{S}(k_x, k_y)$. Furthermore, it is assumed that nuclear spin system is very stable and various factors affecting low-spatial frequency k-space data have the same effect on high-spatial frequency k-space data. The estimated transformation matrix R may be implemented to correct entire synthesized k-space data as in Equation (5) below:

$$S_{corrected}(k_x, k_y) = R \cdot \hat{S}(k_x, k_y) \qquad \text{Equation (5)}$$

where $k_x \in [-k_{max}, k_{max}]$ but $k_y \in [-k_{max}, k_N]$.

In embodiments, the computing device 100 may estimate the transformation matrix based on a part of the first partial k-space dataset and a corresponding part of the second partial k-space dataset. For example, the computing device compares the part 311-1 of the first partial k-space dataset 311 and the part 321-1 of the second partial k-space dataset 321 and estimates the transformation matrix based on the difference between the part 311-1 and the part 321-1. The part 321-1 covers the same area in k-space as the part 311-1 as shown in FIG. 3A, but is created based on the Hermitian Symmetry of the part 311-1 of the first partial k-space dataset 311. In some embodiments, the computing device 100 may acquire a full Fourier k-space dataset for the target area using the MR scanner with a relatively low resolution, e.g., a resolution that is lower than a resolution used for acquiring the first partial k-space dataset 311. Then, the computing device 100 calculates the transformation matrix based on the difference between the full Fourier k-space dataset and the second partial k-space dataset 321.

In step 240, the computing device 100 corrects the second partial k-space dataset using the transformation matrix. The image 330 depicts a synthesized image of the first partial k-space dataset 311 and a part 321-2 of the second partial k-space dataset 321. The computing device 100 may correct the part 321-2 of the image 330 using the transformation matrix.

In step 250, the computing device 100 obtains a full k-space dataset for the target area based on at least one of the corrected second partial k-space dataset, and the first partial k-space dataset. For example, a full k-space dataset of the image 340 in FIG. 3A is obtained by combining the first partial k-space dataset 311 and a corrected partial k-space dataset 341 that is obtained by correcting the part 321-2 using the transformation matrix. Specifically, $S_{acquired}(k_x,k_y)$ ($k_x \in [-k_{max}, k_{max}]$, $k_y \in [-k_N, k_{max}]$) is combined with a part of $S_{corrected}(k_x,k_y)$ ($k_x \in [-k_{max}, k_{max}]$, $k_y \in [-k_{max}, -(k_N+1)]$) to form a full k-space data, as shown in image 340.

In some embodiments, the computing device 100 obtains a full k-space dataset for the target area based on at least one of the corrected second partial k-space dataset, the first partial k-space dataset, and a third k-space dataset. Details of the third k-space dataset will be described below with reference to FIG. 3B. In some embodiments, the full k-space dataset may be filtered by e.g., at least one of hard thresholding, Hamming filtering, Hanning filtering, Blackman filtering, Lanczos filtering, Gaussian filtering, and Wiener filtering.

In step 260, the computing device 100 constructs an image for the target area based on the full k-space dataset. In embodiments, the computing device 100 implements inverse-Fourier transform on the full k-space dataset of the image 340 to construct an image for the target area, e.g., the image 350 in FIG. 3A.

Multi-Dimensional Partial Fourier Acquisition

While one dimensional partial Fourier acquisition is described above, two dimensional partial Fourier acquisition or three dimensional partial Fourier acquisition may be implemented. An exemplary two dimensional partial Fourier acquisition is described below with reference to FIG. 3B. The acquired image may be used for diagnosis, prognosis, surrogate endpoint, or therapeutic response. In some embodiments, the acquired image may be analyzed using computer-aided diagnosis. The computer-aided diagnosis may include a quantification of at least one of volumetric, image intensity, or surface of at least a portion of a region of interest, perfusion, blood volume, flow velocity, relaxation time, diffusion coefficient, proton density, or electro-magnetic properties.

In step 210, the computing device 100 acquires a first partial k-space dataset for a target area of an object using an MRI scanner. For example, as shown in FIG. 1, the computing device 100 receives MR signals from the transmitting and receiving unit 16 and acquires a first partial k-space dataset. In embodiments, the first partial k-space dataset may be acquired in phase-encoding directions. In some embodiments, the first partial k-space dataset is acquired in frequency-encoding directions. In some embodiments, the first partial k-space dataset may be acquired using a combination of partial Fourier acquisition and other under-sampling techniques, such as compressed sensing and parallel imaging acquisitions.

In embodiments, the first partial k-space dataset may be acquired with at least one of $T_1$-weighted spin echo, $T_2$-weighted spin echo, fluid-attenuated inversion-recovery, $T_1$-weighted gradient-echo, $T_2^*$-weighted gradient echo, contrast enhanced $T_1$-weighted gradient echo, contrast enhanced $T_1$-weighted spin echo, diffusion-weighted spin echo, and their variations or combinations.

In embodiments, the first partial k-space dataset may be acquired with imaging sequence including, but not limited to, at least one of two spatial dimensional, three spatial dimensional, or three spatial dimensional plus temporal image acquisition. In some embodiments, the imaging sequence may include at least one of a gradient echo, echo planar or spin echo sequence with or without magnetization preparation, with or without under-sampling techniques, with or without parallel imaging techniques, or with or without Cartesian k-space trajectories In embodiments, the first partial k-space dataset may be acquired using k-space trajectory including at least one of rectilinear, echo planar, but not limited to, radial, Cartesian, non-Cartesian, Zig-Zag, stochastic, rosette, TWIRL, WHIRL and spiral trajectories. The first partial k-space dataset may be acquired according to a k-space sampling order including at least one of a sequential sampling order, a centric sampling order, an interleave sampling order, a reverse sampling order, a random sampling order, or a hybrid sampling order.

The target area may be at least a portion of a subject's body with or without disease. The portion of the subject's body may be at least one of an extremity, brain, spine, neck, chest, breast, joint, prostate, pelvis, or abdomen.

Figure 3B:
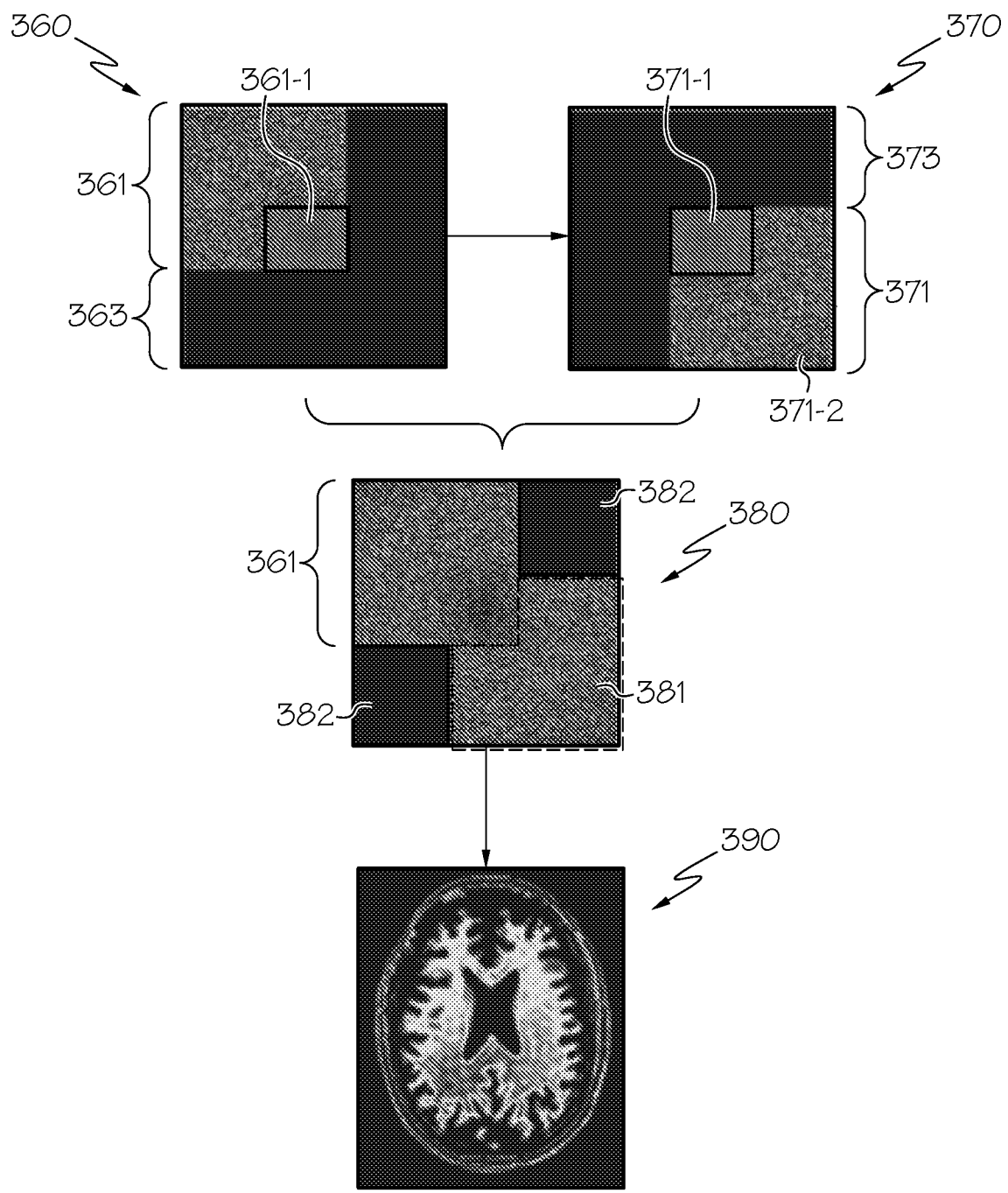
FIG. 3B is a flowchart illustrating a workflow for two-dimensional partial Fourier acquisition reconstruction according to one example in the present disclosure.

The first partial k-space data may be a two dimensional partial Fourier k-space dataset, e.g., a two dimensional partial Fourier k-space dataset 361 of the image 360 in FIG. 3B. Fully sampled 3D k-space data are to be $S(k_x, k_y, k_z)$. $k_x$ is a frequency-encoding and belongs to the full sampling range $[-k_{xmax}, k_{xmax}]$. Both $k_y$ and $k_z$ are two phase-encoding. Their full sampling ranges are $k_y \in [-k_{ymax}, k_{ymax}]$ and $k_z \in [-k_{zmax}, k_{zmax}]$, respectively. In embodiments, partial Fourier acquisition along two phase-encoding directions is considered. As shown in the image 360, partial Fourier acquired data $S_{acquired}(k_y,k_z)$ ($k_y \in [-k_{yN}, k_{ymax}]$ and $k_z \in [-k_{zN}, k_{zmax}]$) are sampled only over the positive spatial frequencies plus a narrow band of low negative spatial frequencies along two phase-encoding directions, where $k_{yN} < k_{ymax}$ and $k_{zN} < k_{zmax}$.

The portion 363 in the image 360 represents portion where k-space data is not acquired by the MRI scanner. In embodiments, the MRI scanner may acquire the first partial k-space dataset with a fraction of less than 0.8. In some embodiments, the MRI scanner may acquire the first partial k-space dataset with a fraction of less than 0.6. In some embodiments, the MRI scanner may acquire the first partial k-space dataset with a fraction of less than 0.4.

In step 220, the computing device 100 creates a second partial k-space dataset for the target area based on Hermitian symmetry of the first partial k-space dataset. Based on the Hermitian symmetry of the first partial k-space dataset as in Equation (2), the second partial k-space dataset for the target area is created. For example, the second partial k-space data may be created, as shown in the partial k-space data set 371 of the image 370 in FIG. 3B. Specifically, the second partial k-space dataset may be obtained by a synthesized $\hat{S}(k_y, k_z)$ using its complex conjugate using Equation (6) below:

$$\hat{S}(k_y,k_z) = S^*_{acquired}(-k_y,-k_z) \qquad \text{Equation (6)}$$

where $k_y \in [-k_{ymax}, k_{yN}]$ but $k_z \in [-k_{zmax}, k_{zN}]$. The missing k-space data are $k_y \in [-k_{ymax}, -(k_{yN}+1)]$ and $k_z \in [-k_{zmax}, -(k_{zN}+1)]$.

Since various factors, such as eddy currents, non-uniform radiofrequency field, non-uniform $B_0$, chemical shift, and motion gradient moments, influence the bias between synthesized k-space data and missing k-space data, it is necessary to correct the synthesized data $\hat{S}(k_y, k_z)$. To achieve this goal, k-space registration is introduced to estimate a transformation matrix, which is described below in step 230. The image 370 includes a portion 373 that is Hermitian Symmetry of the portion 363.

In step 230, the computing device 100 calculates a transformation matrix based on the first partial k-space dataset and the second partial k-space dataset. The transformation matrix may be used to correct the part of second partial k-space dataset for at least one of phase or rotation. The transformation matrix may be estimated from at least one of phase, magnitude, real, and imaginary of an acquired k-space dataset and Hermitian symmetry of the acquired k-space dataset. The transformation matrix in k-space domain may include, but not limited to, at least one of affine transform matrix, rigid transform matrix, linear transform matrix, non-linear transform, and non-rigid transform matrix.

In embodiments, the computing device 100 may estimate the transformation matrix based on a part of the first partial k-space dataset and a corresponding part of the second partial k-space dataset. For example, the computing device compares the part 361-1 of the first partial k-space dataset 361 and the part 371-1 of the second partial k-space dataset 371 and estimates the transformation matrix based on the difference between the part 361-1 and the part 371-1.

It is assumed that the transformation matrix is rigid and includes rotational matrix R and translational vector $\vec{T}$. The transformation matrix may be estimated by the corresponding parts of $S_{acquired}(k_y, k_z)$ and $\hat{S}(k_y, k_z)$ based on Equation (7):

$$\hat{S}(k_y,k_z) = S_{acquired}(R \cdot [k_y,k_z]) \cdot e^{-\pi i (R \cdot [k_y,k_z] \cdot \vec{T})}$$  Equation (7)

where $k_y \in [-k_{yN}, k_{yN}]$ and $k_z \in [-k_{zN}, k_{zN}]$.

According to the Equation (7), the R is estimated from the magnitude k-space data of the corresponding parts of $S_{acquired}(k_x, k_y)$ and $\hat{S}(k_x, k_y)$.

The part 371-1 covers the same area in k-space as the part 361-1 as shown in FIG. 3B, but is created based on the Hermitian Symmetry of the part 361-1 of the first partial k-space dataset 361. In some embodiments, the computing device 100 may acquire a full Fourier k-space dataset for the target area using the MR scanner with a relatively low resolution, e.g., a resolution that is lower than a resolution used for acquiring the first partial k-space dataset 361. Then, the computing device 100 calculates the transformation matrix based on the difference between the full Fourier k-space dataset and the second partial k-space dataset 371.

MRI environments (such as $B_0$ inhomogeneity, chemical shift, susceptibility effect, and motion) introduce an identical displacement of k-space data for both acquired low frequency k-space components and un-acquired high frequency k-space component. That is, MRI environments have the same influences on acquired and un-acquired k-space data. In addition, two dimensional k-space data is acquired with partial Fourier acquisition in a phase encoding direction. As a result, the transform matrix may be estimated from whole or part of the overlapped central k-space data of raw and synthesized data to characterize the displacement of k-space data.

In step 240, the computing device 100 corrects the second partial k-space dataset using the transformation matrix. The computing device 100 may correct the part 371-2 of the image 370 using the transformation matrix. Specifically, k-space dataset may be corrected based on Equation (8) below:

$$S_{corrected}(k_y,k_z) = R \cdot \hat{S}(k_y,k_z)$$  Equation (8)

where $k_y \in [-k_{ymax}, k_{yN}]$ and $k_z \in [-k_{zmax}, k_{zN}]$.

In step 250, the computing device 100 obtains a full k-space dataset for the target area based on at least one of the corrected second partial k-space dataset, the first partial k-space dataset, and a third k-space dataset. For example, a full k-space dataset of the image 380 in FIG. 3B is obtained by combining the first partial k-space dataset 361, a dataset 381 that is obtained by correcting the part 371-2 using the transformation matrix, and third k-space dataset 382. The third k-space dataset 382 may be zero-filling data. The third k-space dataset 382 includes k-space data that is outside the boundary of the first k-space dataset 361 or the second k-space dataset 371 as shown in FIG. 3B. Specifically, $S_{acquired}(k_y,k_z)$ ($k_y \in [-k_{yN}, k_{ymax}]$ and $k_z \in [-k_{zN}, k_{zmax}]$), which corresponds to the first partial k-space dataset (i.e., the part 361 in FIG. 3B), is combined with a part of $S_{corrected}(k_y,k_z)$ $\{(k_y \in [-k_{ymax}, k_{yN}], k_z \in [-k_{zmax}, -(k_{zN}+1)]) \& k_y \in [-k_{ymax}, -(k_{yN}+1)] k_z \in [-k_{zN}, k_{zN}]\}$, which corresponds to the corrected second partial k-space dataset (i.e., the part 381 in FIG. 3B), and zeros $\{(k_y \in [-k_{ymax}, -(k_{yN}+1)] k_z \in [(k_{zN}+1), k_{zmax}]) \& (k_y \in [(k_{yN}+1), k_{ymax}], k_z \in [-k_{zmax}, -(k_{zN}+1)])\}$, which corresponds to the parts 382 in FIG. 3B, to form a full k-space data, as the image 380.

In some embodiments, the full k-space dataset may be filtered by e.g., at least one of hard thresholding, Hamming filtering, Hanning filtering, Blackman filtering, Lanczos filtering, Gaussian filtering, and Wiener filtering.

In step 260, the computing device 100 constructs an image for the target area based on the full k-space dataset. In embodiments, the computing device 100 implements inverse-Fourier transform on the full k-space dataset to construct an image for the target area, e.g., the image 390 in FIG. 3B. The acquired image may be used for diagnosis, prognosis, surrogate endpoint, or therapeutic response. In some embodiments, the acquired image may be analyzed using computer-aided diagnosis. The computer-aided diagnosis may include a quantification of at least one of volumetric, image intensity, or surface of at least a portion of a region of interest, perfusion, blood volume, flow velocity, relaxation time, diffusion coefficient, proton density, or electro-magnetic properties.

In some embodiments, partial Fourier acquisition may further combine with using at least one of imaging techniques including at least one of parallel imaging technique, under-sampling technique including compressed sensing technique, or simultaneous multi-slice imaging technique. Partial Fourier acquisition reconstruction may be separated with other image reconstruction, such as image reconstruction of at least one of parallel imaging technique, under-sampling technique including compressed sensing technique, or simultaneous multi-slice imaging technique.

Most existing techniques are one-dimensional or two-dimensional in nature. That is, the correction corrects for errors only along phase encoding direction. These techniques assume that the corrections are independent of frequency encoding direction. However, the failure of conjugate symmetry synthesized data are two dimensional or three dimensional in nature, and, therefore, a two-dimensional or three dimensional correction is required. That is, the correction should correct for errors along phase encoding directions and a frequency, encoding direction. For example, partial. Fourier acquisition along a frequency encoding direction is very important for reducing echo time TE in functional MRI and diffusion weighted imaging.

Image Evaluation

To evaluate the image quality of the reconstructed images, the distribution of error in magnitude between the reconstructed and reference images at each pixel are compared visually and quantitatively using the ratio of the root mean square error (RMSE) to the sum of the signal intensity of a reference image. RMSE is defined as:

$$RMSE = \frac{\sqrt{\sum (I_{rec} - I_{ref})^2}}{\sum I_{ref}}$$

where/ref is the reference image reconstructed from full k-space and/re, is the image reconstructed from partial k-space acquisition (e.g., the image 350 in FIG. 3A or the image 390 in FIG. 3B). RMSE results from image noise, artifacts and resolution.

One Dimensional Phase Encoding Partial Fourier Acquisition

Example 1: $T_1$-Weighted Gradient Echo Brain Imaging

Figure 4:
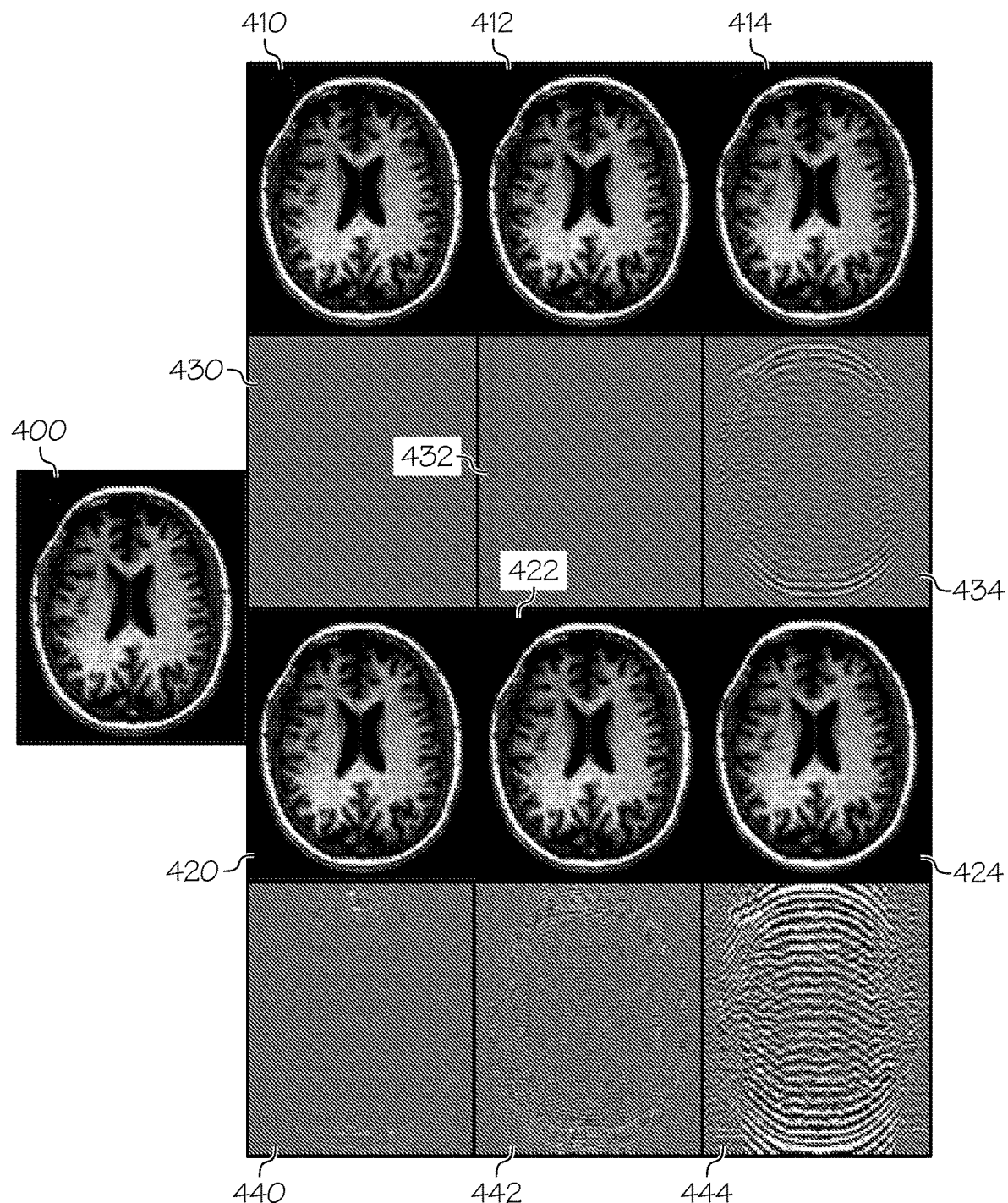
FIG. 4 shows an example of brain images of a healthy subject acquired with $T_1$-weighted FSPGR sequence and their difference between the reconstructed images from full and one-dimensional phase-encoding partial k-space data.

A brain image was obtained using inversion preparation fast spoiled grass sequence (IR-FSPGR) sequence with FOV 200×200 mm$^2$, matrix 256×256, slice thickness 1.0 mm, echo space time 7.8 milliseconds (ms), flip angle of 12°, inversion recovery time 450 ms, slice number 154, echo time (TE) 3.0 ms, minimal repetition time (TR). FIG. 4 shows brain images of a healthy subject acquired with $T_1$-weighted FSPGR sequence and their difference between the reconstructed images from full and partial k-space data.

An image 400 reconstructed by full k-space dataset is used as a reference. The images 410, 412, 414 are reconstructed from partial k-space dataset according to the present method. The image 410 is reconstructed from partial k-space dataset at the k-space coverage of 87.7%. The image 412 is reconstructed from partial k-space dataset at the k-space coverage of 75%. The image 414 is reconstructed from partial k-space dataset at the k-space coverage of 62.5%. The images 420, 422, 424 are reconstructed from partial k-space dataset using zero-filling. Images 430, 432, 434 show difference between the image 400 and the images 410, 412, 414, respectively. Images 440, 442, 444 show difference between the image 400 and the images 420, 422, 424, respectively.

All images reconstructed by the present method are clearer and sharper than those reconstructed by zero-filling at the corresponding k-space coverage. Additionally, no little error is observed in the difference between the images 410, 412 reconstructed according to the present method and the image 400 reconstructed based on the fully sampled k-.

Quantitative analysis indicates the RMSEs of images 410, 412, 414 relative to the image 400 reconstructed from the fully sampled k-space data are much lower than images 420, 422, 424 using zero-filling method as shown in Table 1 below.

The RMSEs of images 410, 412, 414 obtained based on the present method are 0.049%, 0.12% and 1.1% at the k-space coverage of 87.7%, 75% and 62.5%, respectively. The RMSEs of images 420, 422, 424 obtained based on the zero-filling method are 1.9%, 4.4% and 9.7%, respectively. Thus, the present method provides more accurate images than zero filling based partial Fourier reconstruction method in the brain imaging with $T_1$-weighted magnetization preparation gradient echo sequence.

Example 2: $T_2$-Weighted Fast Spin Echo Brain Imaging

Figure 5:
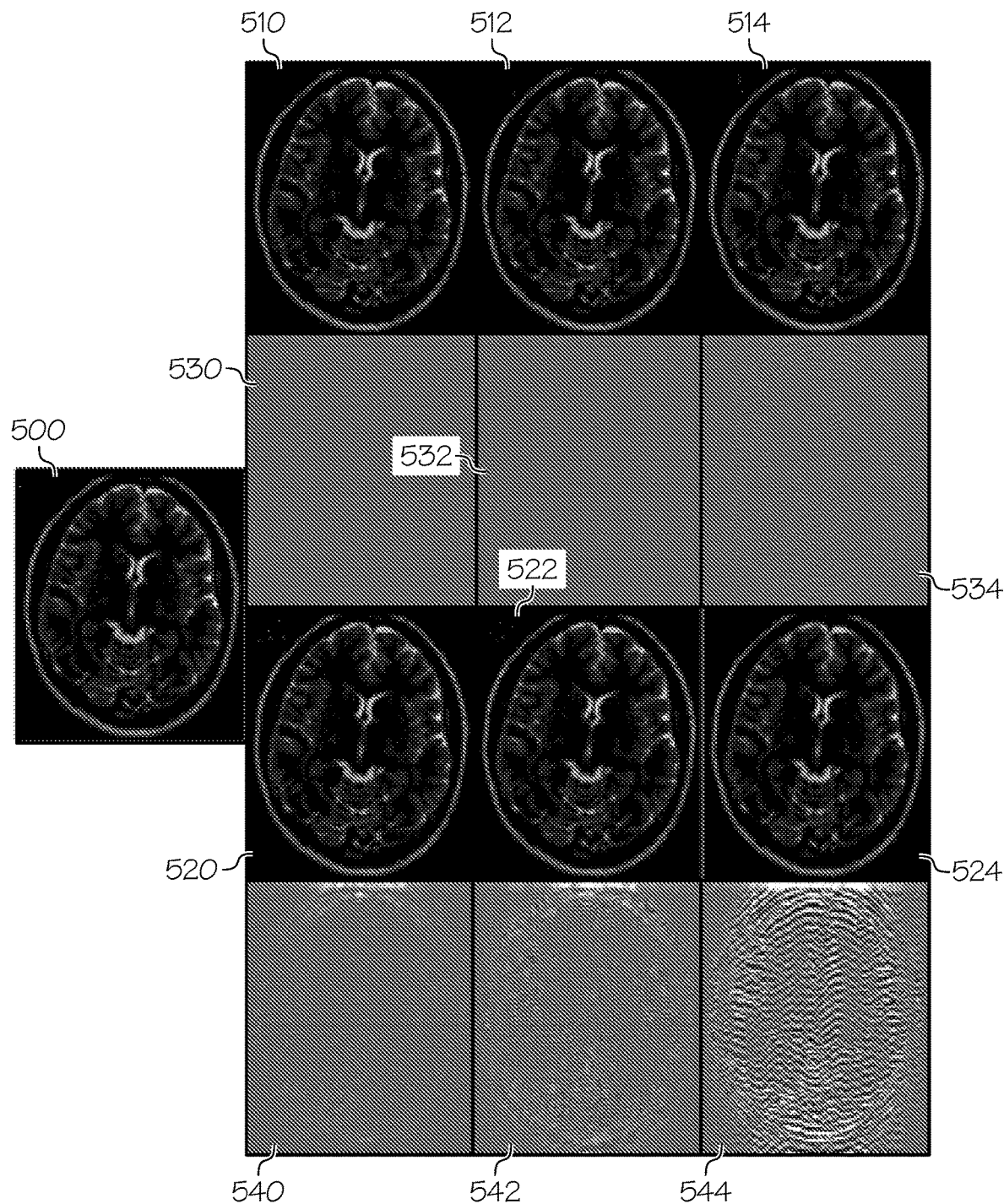
FIG. 5 shows an example of brain images of a healthy subject acquired with $T_2$-weighted fast spin echo sequence and their difference between the reconstructed images from full and one-dimensional phase-encoding partial k-space data.

A brain image was obtained using fast spin echo $T_2$-weighted sequence with FOV 256×256 mm$^2$, matrix 256×256, echo train length 13, slice thickness 3 mm, slice number 56, TE 100 ms, and TR 3000 ms. FIG. 5 showed brain images of a healthy subject acquired with brain images of a healthy subject acquired with $T_2$-weighted fast spin echo sequence and their difference between the reconstructed images from full and partial k-space data.

An image 500 reconstructed by full k-space dataset is used as a reference. The images 510, 512, 514 are reconstructed from partial k-space dataset according to the present method. The image 510 is reconstructed from partial k-space dataset at the k-space coverage of 87.7%. The image 512 is reconstructed from partial k-space dataset at the k-space coverage of 75%. The image 514 is reconstructed from partial k-space dataset at the k-space coverage of 62.5%. The images 520, 522, 524 are reconstructed from partial k-space dataset using zero-filling. Images 530, 532, 534 show difference between the image 500 and the images 510, 512, 514, respectively. Images 540, 542, 544 show difference between the image 500 and the images 520, 522, 524, respectively.

As expected, all images reconstructed by the present method show a better quality over those reconstructed by zero-filling at the corresponding k-space coverage. No little error is observed in the difference between the images 510, 512, 514 and the image 500. In Table 1 above, the RMSEs of the images 510, 512, 514 are 0.044%, 0.11% and 0.25%, respectively, and the RMSEs of the images 520, 522, 524 are 1.7%, 4.1% and 7.7%, at the k-space coverage of 87.7%, 75% and 62.5%, respectively. Thus, the present method provides more accurate images than zero filling based partial Fourier reconstruction method in the brain imaging acquired with $T_2$-weighted fast spin echo sequence.

Example 3: Fluid-Attenuated Inversion Recovery (FLAIR) $T_2$-Weighted Brain Imaging A brain image was obtained using FLAIR $T_2$-weighted sequence with FOV 256×256 mm$^2$, matrix 256×256, slice thickness 3 mm, slice number 60, TE 83 ms, TR 9000 ms and inversion recovery time 2500 ms. Brain images of a

TABLE 1

Figure 6:
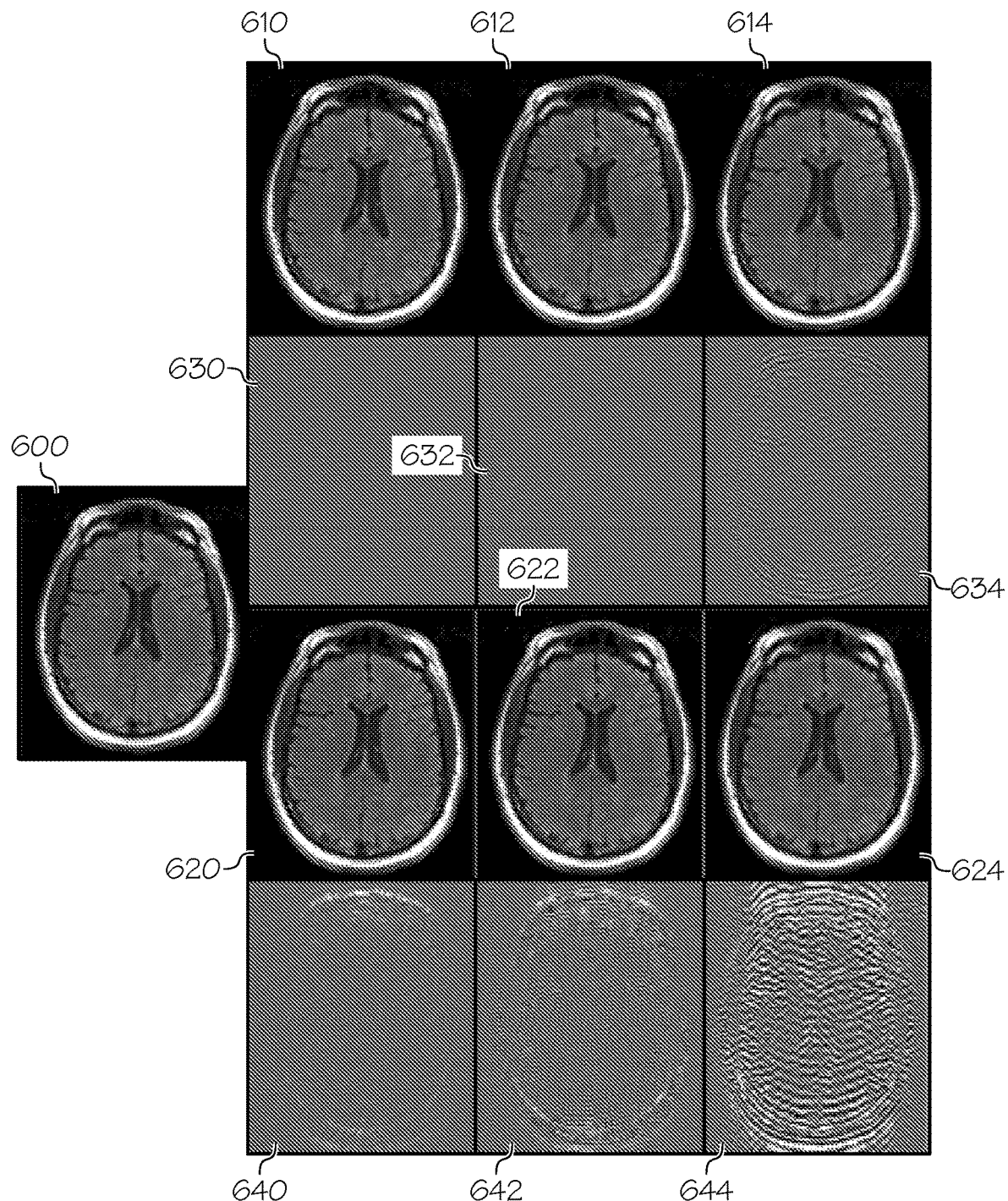
FIG. 6 shows an example of brain images of a healthy subject acquired with fluid-attenuated inversion recovery $T_2$-weighted sequence and their difference between the reconstructed images from full and one-dimensional phase-encoding partial k-space data.

| | RMSE | | | | | |
|---|---|---|---|---|---|---|
| k-space coverage | 62.5% | | 75% | | 87.7% | |
| Sequence | Zero-filling | Present method | Zero-filling | Present method | Zero-filling | Present method |
| IR-FSPGR | 0.097 | 0.011 | 0.044 | 0.0012 | 0.019 | 4.9E−4 |
| T2-FSE | 0.077 | 0.003 | 0.041 | 0.0011 | 0.017 | 4.4E−4 |
| T2_FLAIR | 0.074 | 0.006 | 0.043 | 6.2E−4 | 0.021 | 1.80E−4 |
| DWI (b = 0) | 0.075 | 0.002 | 0.022 | 1.20E−4 | 0.002 | 5.80E−5 |
| DWI(b = 1000) | 0.036 | 0.003 | 0.018 | 7.10E−4 | 0.009 | 3.10E−4 |
| SWAN | 0.23 | 0.24 | 0.007 | 0.008 | 0.001 | 0.0015 | healthy subject acquired with brain images of a healthy subject acquired with a fluid-attenuated inversion recovery $T_2$-weighted fast spin echo sequence and their difference between the reconstructed images from full and partial k-space data are shown in FIG. 6.

An image 600 reconstructed by full k-space dataset is used as a reference. The images 610, 612, 614 are reconstructed from partial k-space dataset according to the present method. The image 610 is reconstructed from partial k-space dataset at the k-space coverage of 87.7%. The image 612 is reconstructed from partial k-space dataset at the k-space coverage of 75%. The image 614 is reconstructed from partial k-space dataset at the k-space coverage of 62.5%. The images 620, 622, 624 are reconstructed from partial k-space dataset using zero-filling. Images 630, 632, 634 show difference between the image 600 and the images 610, 612, 614, respectively. Images 640, 642, 644 show difference between the image 600 and the images 620, 622, 624, respectively.

All images reconstructed by the present method outperform those reconstructed by zero-filling at the corresponding k-space coverage. No little error is observed in the difference between the images 610, 612, 614 and the image 600. In Table 1, the RMSEs of the images 610, 612, 614 obtained based on the present method are less than 1.0% at all three different k-space coverages. However, the RMSEs of the images 620, 622, 624 obtained based on zero-filling method are more than 2.1% at these k-space coverages. Thus, the present method provides more accurate images than zero filling based partial Fourier reconstruction method in the brain imaging acquired with a fluid-attenuated inversion recovery $T_2$-weighted fast spin echo sequence.

Example 4. $T_2$*-Weighted Brain Imaging

Figure 7:
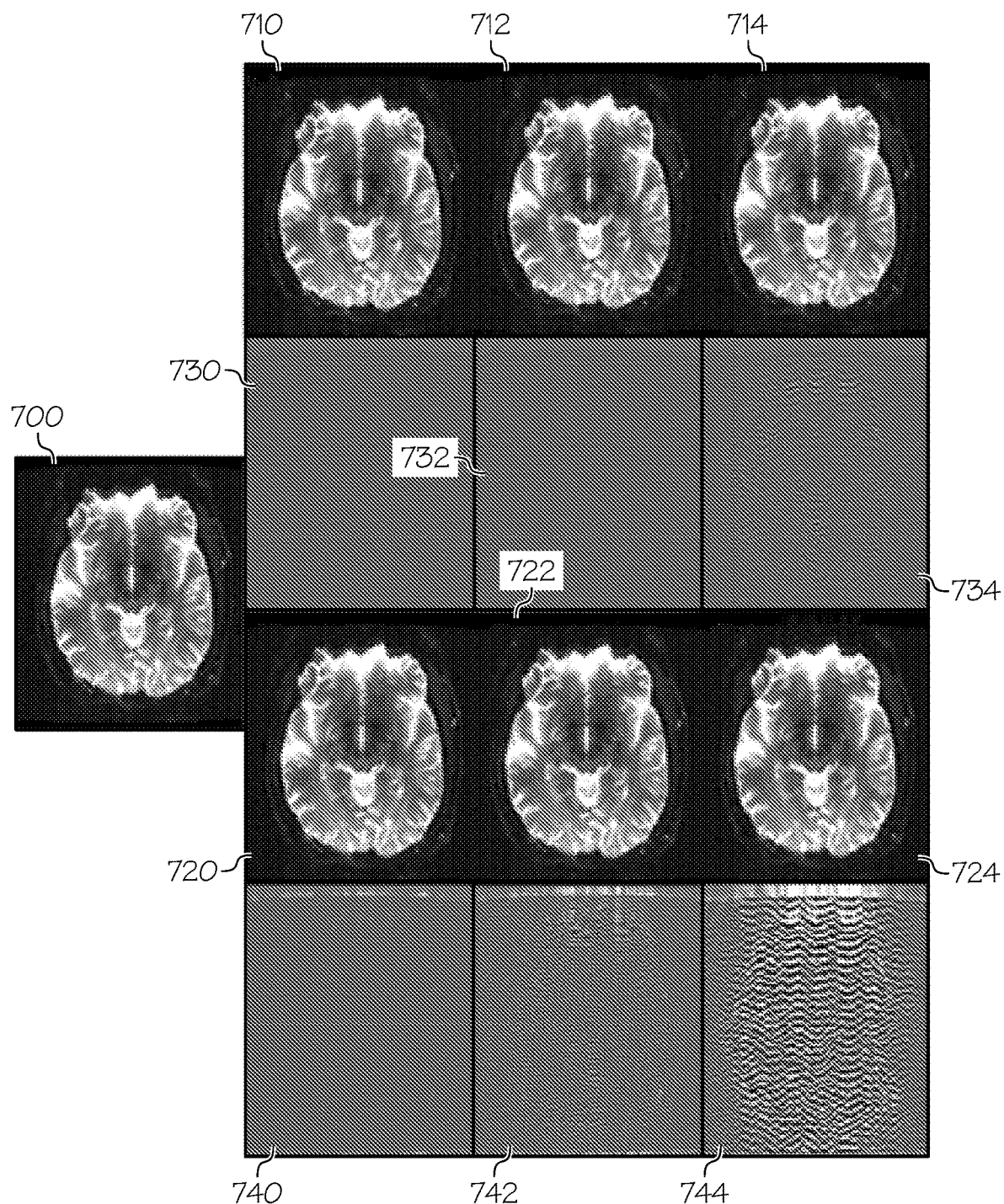
FIG. 7 shows an example of brain images of a healthy subject acquired with $T_2$*-weighted echo planar spin echo imaging sequence and their difference between the reconstructed images from full and one-dimensional phase-encoding partial k-space data.

A $T_2$*-weighted brain image of a healthy subject is acquired by spin-echo echo planar imaging (EPI) sequence with FOV 240×240 mm$^2$, matrix 132×160, slice thickness 4 mm, TR 8100 ms, and TE 73 ms. FIG. 7 showed brain images reconstructed by the present method and zero-filling and their difference between the reconstructed images from full and partial k-space data.

An image 700 reconstructed by full k-space dataset is used as a reference. The images 710, 712, 714 are reconstructed from partial k-space dataset according to the present method. The image 710 is reconstructed from partial k-space dataset at the k-space coverage of 87.7%. The image 712 is reconstructed from partial k-space dataset at the k-space coverage of 75%. The image 714 is reconstructed from partial k-space dataset at the k-space coverage of 62.5%. The images 720, 722, 724 are reconstructed from partial k-space dataset using zero-filling. Images 730, 732, 734 show difference between the image 700 and the images 710, 712, 714, respectively. Images 740, 742, 744 show difference between the image 700 and the images 720, 722, 724, respectively.

All images reconstructed by the present method have a better quality over those reconstructed by zero-filling at the corresponding k-space coverage. No little error is observed in the difference between the images 710, 712, 714 and the image 700. In Table 1, the RMSEs of the images 710, 712, 714 are 0.0058%, 0.012% and 0.2% obtained based on the present method, and the RMSEs of the images 720, 722, 724 are 0.2%, 2.2% and 7.5%, at the k-space coverage of 87.5%, 75% and 62.5%, respectively. Thus, the present method provides more accurate images than zero filling method in the brain imaging acquired with diffusion weighted imaging sequence.

Example 5. Diffusion-Weighted Brain Imaging

Figure 8:
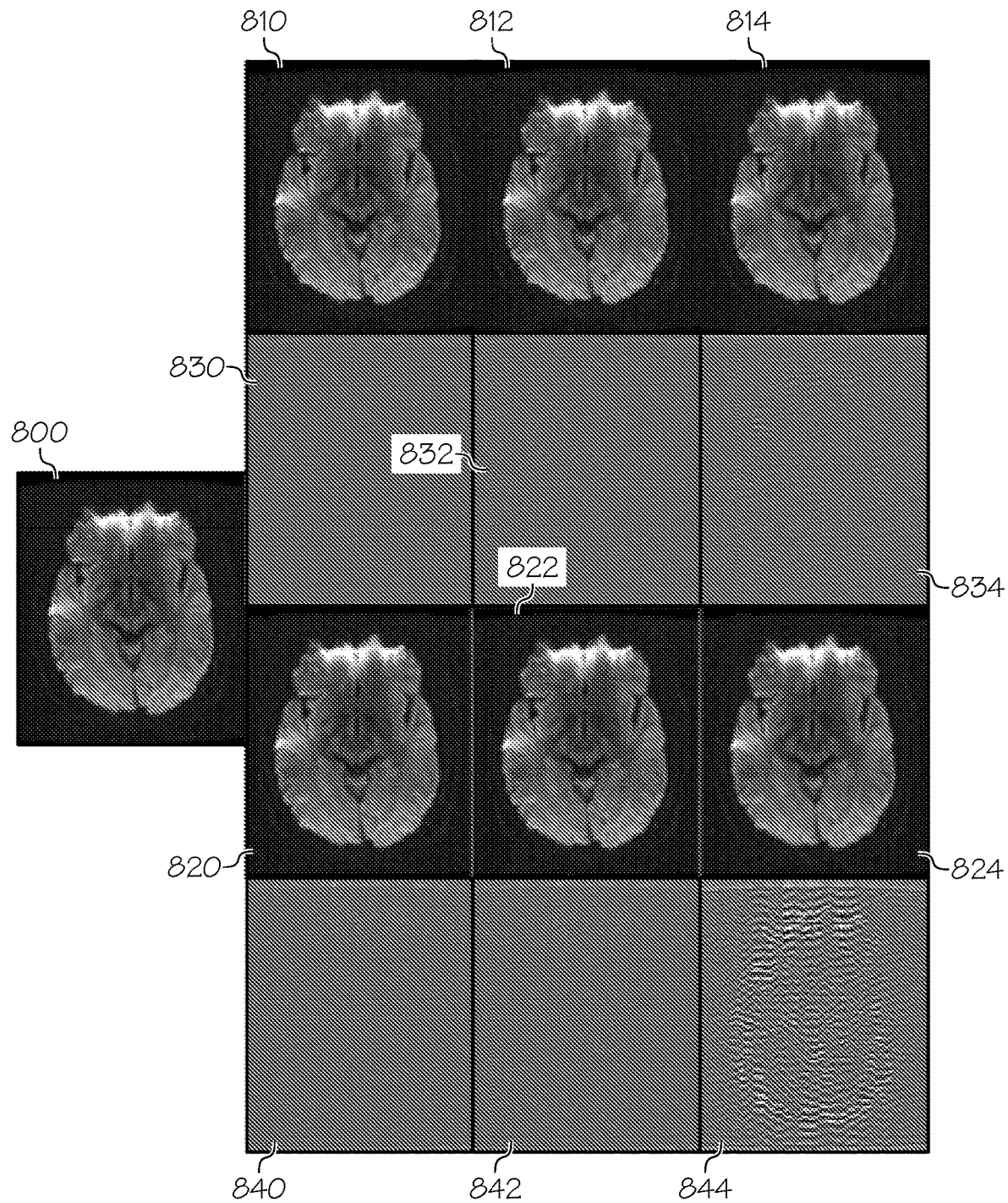
FIG. 8 shows an example of brain images of a healthy subject acquired with diffusion-weighted sequence at $b=1000$ s/mm$^2$ and their difference between the reconstructed images from full and one-dimensional phase-encoding partial k-space data.

A diffusion-weighted brain image is acquired by spin-echo echo planar imaging sequence with FOV 240×240 mm$^2$, matrix 132×160, slice thickness 4 mm, TR 8100 ms, TE 73 ms, and b value=1000 s/mm$^2$. FIG. 8 shows brain images of a healthy subject acquired with brain images of a healthy subject acquired with diffusion-weighted EPI sequence (b=1000 s/mm$^2$) their difference between the reconstructed images from full and partial k-space data.

An image 800 reconstructed by full k-space dataset is used as a reference. The images 810, 812, 814 are reconstructed from partial k-space dataset according to the present method. The image 810 is reconstructed from partial k-space dataset at the k-space coverage of 87.7%. The image 812 is reconstructed from partial k-space dataset at the k-space coverage of 75%. The image 814 is reconstructed from partial k-space dataset at the k-space coverage of 62.5%. The images 820, 822, 824 are reconstructed from partial k-space dataset using zero-filling. Images 830, 832, 834 show difference between the image 800 and the images 810, 812, 814, respectively. Images 840, 842, 844 show difference between the image 800 and the images 820, 822, 824, respectively.

All images reconstructed by the present method have a better quality over those reconstructed by zero-filling at the corresponding k-space coverage. No little error is observed in the difference between the images 810, 812, 814 and the image 800. In Table 1, the RMSEs of the images 810, 812, 814 obtained based on the present method are 0.031%, 0.071% and 0.34%, and the RMSEs of the images 820, 822, 824 obtained based on zero-filling are 3.5%, 1.8% and 0.94%, at the k-space coverage of 87.5%, 75% and 62.5%, respectively. Thus, the present method provides more accurate images than zero filling method in the brain imaging acquired with diffusion weighted imaging sequence.

Two Dimensional Phase Encoding Partial Fourier Acquisition

Example 6: 3 Dimensional $T_1$-Weighted Gradient Echo Brain Imaging

Figure 9:
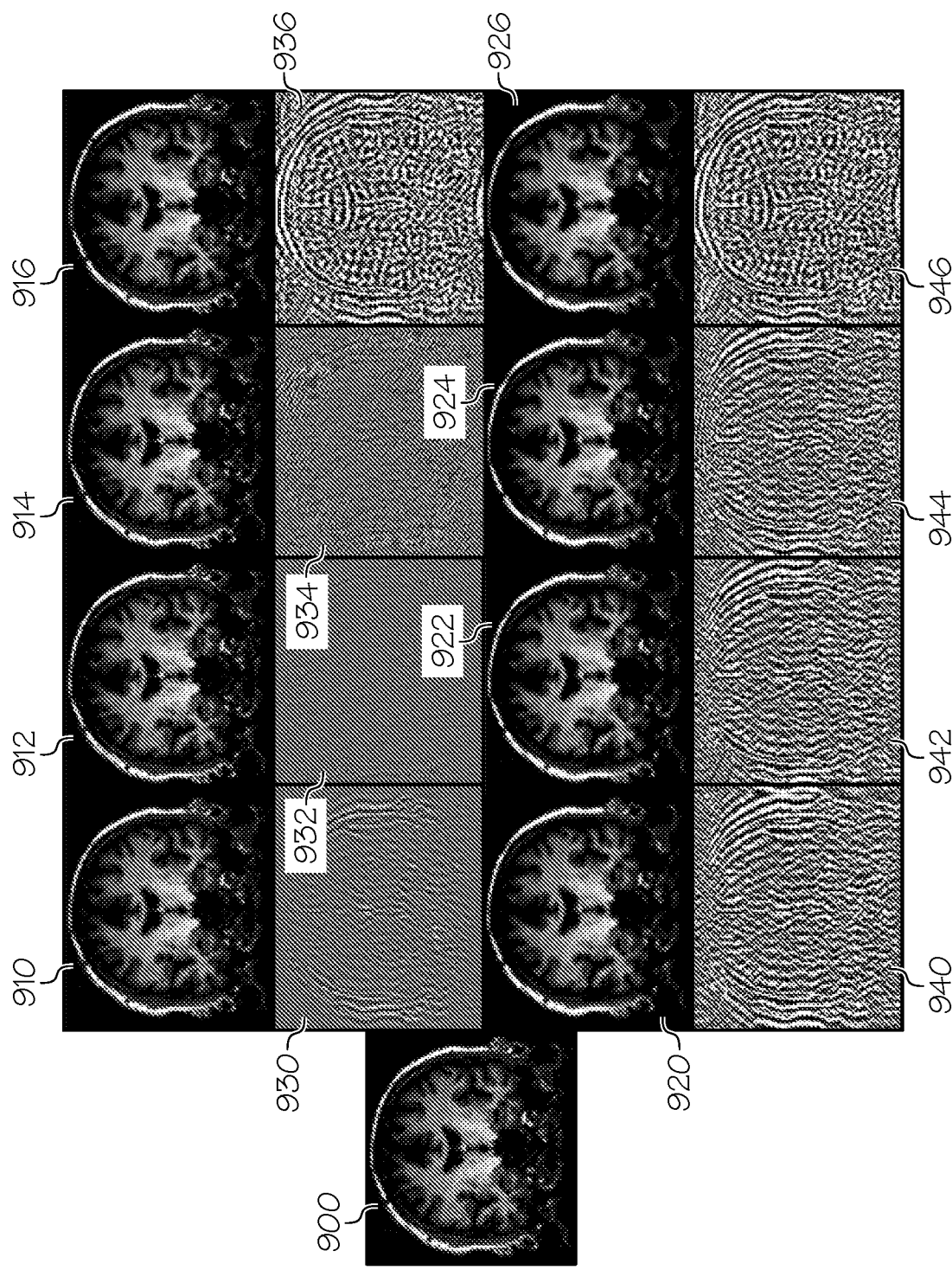
FIG. 9 shows an example of brain images of a healthy subject acquired with $T_1$-weighted FSPGR sequence and their difference between the reconstructed images from full and two dimensional phase-encoding partial k-space data.

A brain image was obtained using 3 dimensional inversion preparation fast spoiled grass sequence (IR-FSPGR) sequence with FOV 200×200 mm$^2$, matrix 256×256, slice thickness 1.0 mm, echo space time 7.8 ms, flip angle of 12°, inversion recovery time 450 ms, slice number 154, echo time (TE) 3.0 ms, minimal repetition time (TR). FIG. 9 shows brain images of a healthy subject acquired with $T_1$-weighted FSPGR sequence and their difference between the reconstructed images from full and partial k-space data. The partial Fourier acquisition was formed by removing a part of full k-space data.

The image 900 reconstructed by full k-space is used as a reference. The images 910, 912, 914, 916 are reconstructed from partial k-space dataset according to the present method. The image 910 is reconstructed from partial k-space dataset at the k-space coverage of 62.5%. The image 912 is reconstructed from partial k-space dataset at the k-space coverage of 55%. The image 914 is reconstructed from partial k-space dataset at the k-space coverage of 47%. The image 916 is reconstructed from partial k-space dataset at the k-space coverage of 39%. The images 920, 922, 924, 926 are reconstructed from partial k-space dataset using zero-filling. Images 930, 932, 934, 936 show difference between the image 900 and the images 910, 912, 914, 916, respectively. Images 940, 942, 944, 946 show difference between the image 900 and the images 920, 922, 924, 926, respectively.

Two dimensional phase encoding partial Fourier acquisition are performed at one dimensional phase encoding k-space coverage of 62.5% and other phase encoding k-space coverage of 1, 87.5%, 75% and 62.5%, respectively. That is, total two phase encoding k-space coverage of 62.5%, 55%, 47% and 39%, respectively, is implemented. The images 910, 912, 914, 916 reconstructed by the present method are clearer and sharper that the images 920, 922, 924, 926 reconstructed by zero-filling at the corresponding k-space coverage. Quantitative analysis indicated the RMSE of images relative to the images reconstructed from the fully sampled k-space data using the present method is much lower than that using zero-filling method as shown in Table 2 below.

between the image 1000 and the images 1010, 1012, 1014, 1016, respectively. Images 1040, 1042, 1044, 1046 show difference between the image 1000 and the images 1020, 1022, 1024, 1026, respectively.

Two dimensional phase encoding partial Fourier acquisition are performed at one dimensional phase encoding k-space coverage of 62.5% and other phase encoding k-space coverage of 100%, 87.5%, 75% and 62.5%, respectively. That is, total two phase encoding k-space coverage of 62.5%, 55%, 47% and 39%, respectively. The images 1010, 1012, 1014, 1016 reconstructed by the present method are clearer and sharper than the images 1020, 1022, 1024, 1026 reconstructed by zero-filling at the corresponding k-space coverage. Quantitative analysis indicated the RMSEs of the images 1010, 1012, 1014, 1016 relative to the image 1000 reconstructed from the fully sampled k-space data are much lower than RMSEs of the images 1020, 1022, 1024, 1026 obtained using zero-filling method as shown in Table 2. The RMSEs of the images 1010, 1012, 1014, 1016 are 0.14%,

TABLE 2

| K-space coverage | RMSE | | | | | | | |
|---|---|---|---|---|---|---|---|---|
| | 62.5% | | 55% | | 47% | | 39% | |
| Sequence | Zero-filling | Present method | Zero-filling | Present method | Zero-filling | Present method | Zero-filling | Present method |
| IR-FSPGR | 0.083 | 0.012 | 0.087 | 0.025 | 0.11 | 0.043 | 0.12 | 0.072 |
| T2-FSE-Cube | 0.089 | 0.0014 | 0.09 | 0.0058 | 0.09 | 0.0089 | 0.11 | 0.046 |
| T2_FLAIR Cube | 0.021 | 5.70E−04 | 0.022 | 0.002 | 0.024 | 0.0037 | 0.51 | 0.013 |

The RMSEs of the images 910, 912, 914, 916 are 1.2%, 2.5%, 4.3% and 7.2% at the k-space coverage of 62.5%, 55%, 47% and 39%, respectively. The RMSEs of the images 940, 942, 944, 946 are 8.3%, 8.7%, 11%, and 12%, respectively. Thus, the present method provides more accurate images than zero filling based partial Fourier reconstruction method in the brain imaging with $T_1$-weighted magnetization preparation gradient echo sequence.

Example 7: 3 Dimensional $T_2$-Weighted Fast Spin Echo

Figure 10:
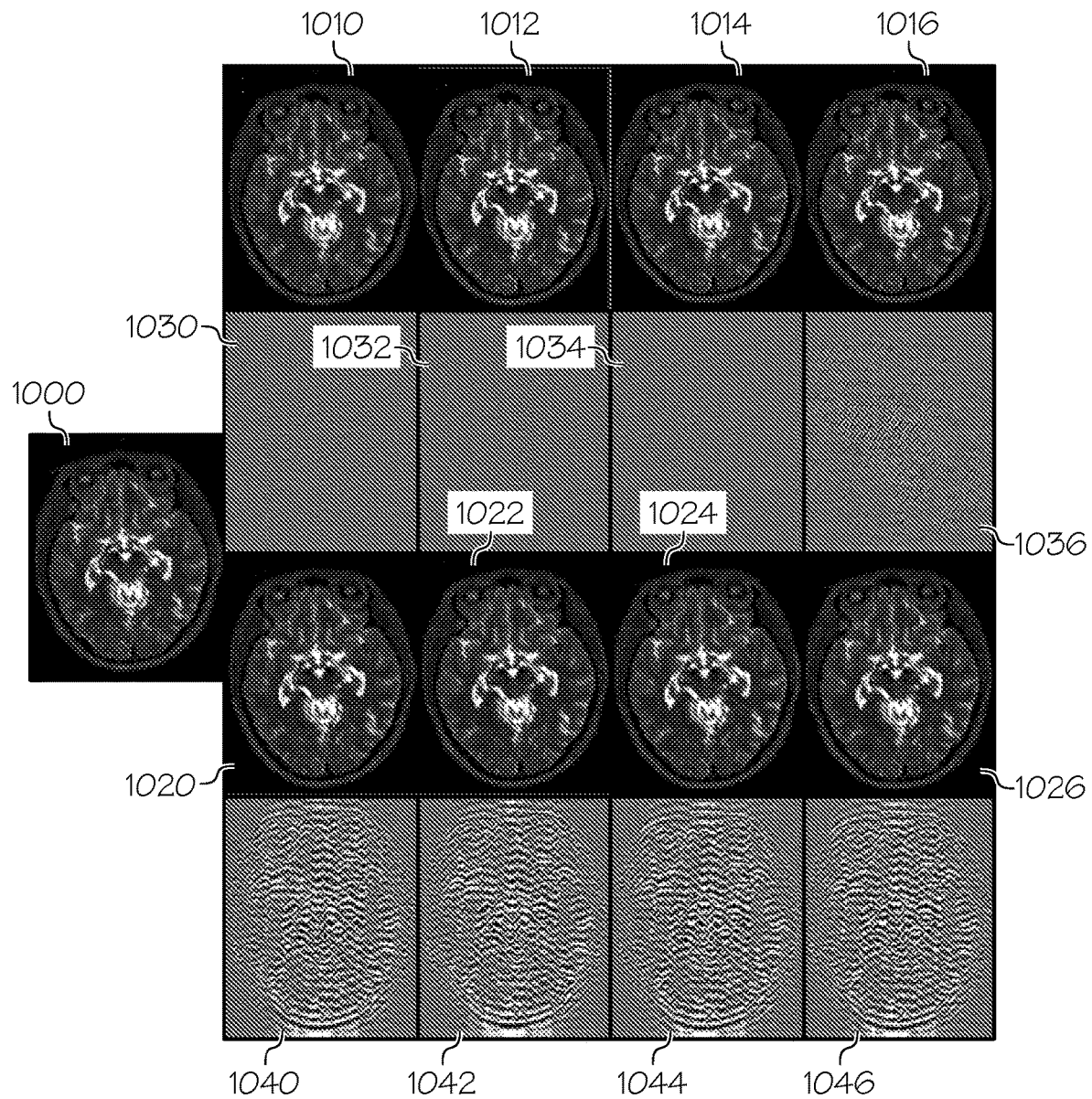
FIG. 10 shows an example of brain images of a healthy subject acquired with $T_2$-weighted fast spin echo sequence and their difference between the reconstructed images from full and two dimensional phase-encoding partial k-space data.

A brain image is obtained using 3 dimensional fast spin echo T-weighted sequence with FOV 256×256 mm², matrix 256×256, echo train length 160, slice thickness 1 mm, slice number 167, TE 113 ms, and TR 3000 ms. FIG. 10 shows an example of brain images of a healthy subject acquired with $T_2$-weighted fast spin echo sequence and their difference between the reconstructed images from full and two dimensional phase-encoding partial k-space data. The image 1000 reconstructed by full k-space is used as a reference. The partial Fourier acquisition was formed by removing a part of full k-space data.

The images 1010, 1012, 1014, 1016 are reconstructed from partial k-space dataset according to the present method. The image 1010 is reconstructed from partial k-space dataset at the k-space coverage of 62.5%. The image 1012 is reconstructed from partial k-space dataset at the k-space coverage of 55%. The image 1014 is reconstructed from partial k-space dataset at the k-space coverage of 47%. The image 1016 is reconstructed from partial k-space dataset at the k-space coverage of 39%. The images 1020, 1022, 1024, 1026 are reconstructed from partial k-space dataset using zero-filling. Images 1030, 1032, 1034, 1036 show difference 0.58%, 0.89% and 4.6% at the k-space coverage of 62.5%, 55%, 47% and 39%, respectively. The RMSEs of the images 1020, 1022, 1024, 1026 are 8.9%, 9.0%, 9.0%, and 11%, respectively. Thus, the present method provides more accurate images than zero filling based partial Fourier reconstruction method in the brain imaging with $T_1$-weighted magnetization preparation fast spin echo sequence.

Figure 11:
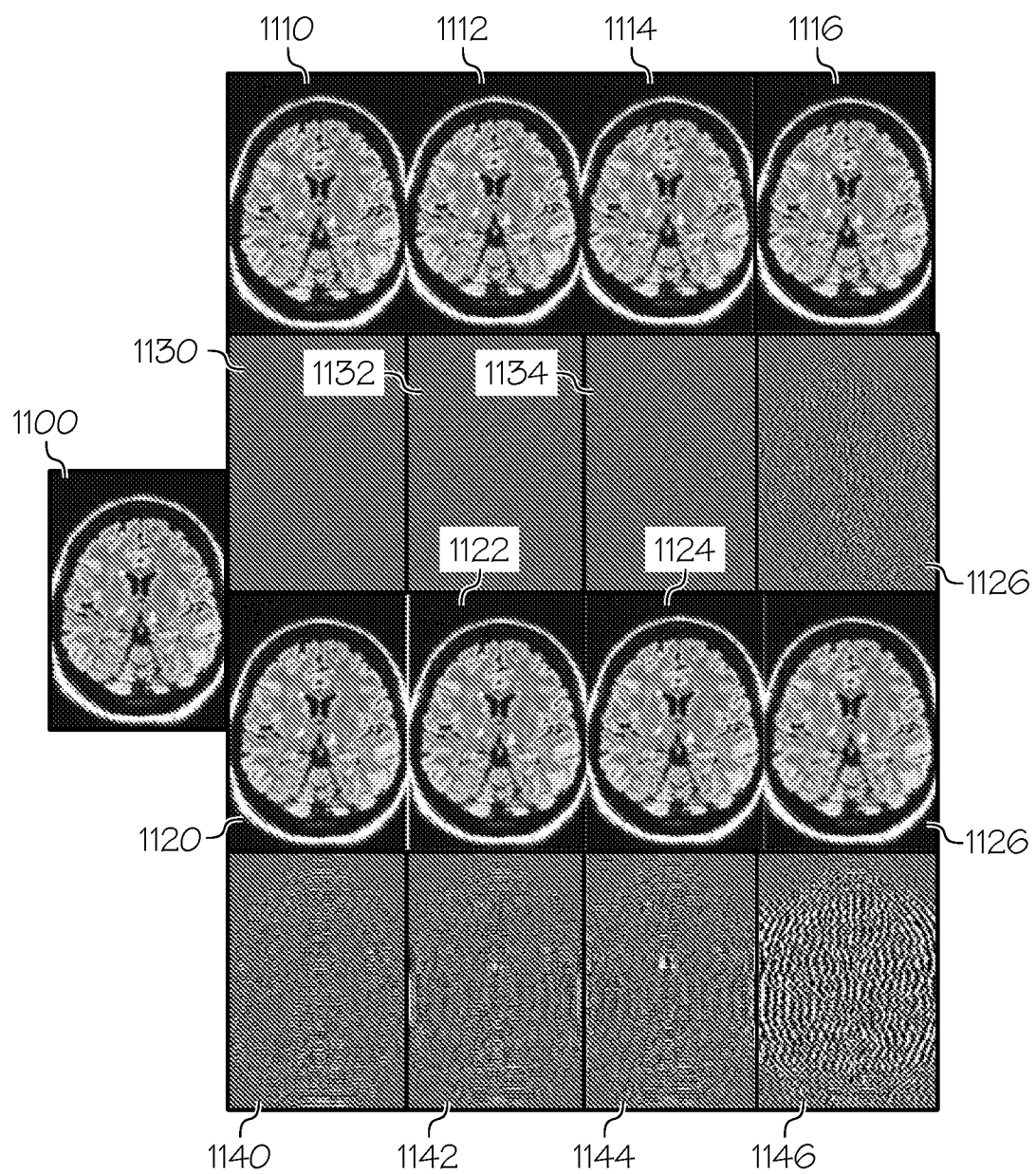
FIG. 11 shows an example of brain images of a healthy subject acquired with fluid-attenuated inversion recovery $T_2$-weighted sequence and their difference between the reconstructed images from full and two dimensional phase-encoding partial k-space data.

Example 8: 3 Dimensional Fluid-Attenuated Inversion Recovery (FLAIR) $T_2$-Weighted Brain Imaging A brain image was obtained using 3 dimensional fast spin echo T-weighted sequence with FOV 256×256 mm², matrix 256×256, echo train length 180, slice thickness 1.0 mm, slice number 168, TE 104 ms, inversion recovery time 1790 ms, and TR 6300 ms. FIG. 11 shows an example of brain images of a healthy subject acquired with 3 dimensional Fluid-attenuated inversion recovery $T_2$-weighted fast spin echo sequence and their difference between the reconstructed images from full and two dimensional phase-encoding partial k-space data. The image 1100 recontructed by full k-space is used as a reference. The partial Fourier acquisition is formed by removing a part of full k-space data.

The images 1110, 1112, 1114, 1116 are reconstructed from partial k-space dataset according to the present method. The image 1110 is reconstructed from partial k-space dataset at the k-space coverage of 62.5%. The image 1112 is reconstructed from partial k-space dataset at the k-space coverage of 55%. The image 1114 is reconstructed from partial k-space dataset at the k-space coverage of 47%. The image 1116 is reconstructed from partial k-space dataset at the k-space coverage of 39%. The images 1120, 1122, 1124, 1126 are reconstructed from partial k-space dataset using zero-filling. Images 1130, 1132, 1134, 1136 show difference between the image 1100 and the images 1110, 1112, 1114, 1116, respectively. Images 1140, 1142, 1144, 1146 show difference between the image 1100 and the images 1120, 1122, 1124, 1126, respectively.

Two dimensional phase encoding partial Fourier acquisition are performed at one dimensional phase encoding k-space coverage of 62.5% and other phase encoding k-space coverage of 1, 87.5%, 75% and 62.5%, respectively. That is, total two phase encoding k-space coverage of 62.5%, 55%, 47% and 39%, respectively. The images 1110, 1112, 1114, 1116 reconstructed by the present method are clearer and sharper than the images 1120, 1122, 1124, 1126 reconstructed by zero-filling at the corresponding k-space coverage. Quantitative analysis indicates the RMSEs of the images 1110, 1112, 1114, 1116 relative to the image 1000 reconstructed from the fully sampled k-space data are much lower than the RMSEs of the images 1120, 1122, 1124, 1126 using zero-filling method in Table 2. The RMSEs of the images 1110, 1112, 1114, 1116 are 0.057%, 0.2%, 0.37% and 1.3% at the k-space coverage of 62.5%, 55%, 47% and 39%, respectively. The RMSEs of the images 1120, 1122, 1124, 1126 are 2.1%, 2.2%, 2.4%, and 51%, respectively. Thus, the present method provides more accurate images than zero filling based partial Fourier reconstruction method in the brain imaging with FLAIR $T_2$-weighted magnetization preparation gradient echo sequence.

One Dimensional Phase-Encoding and One Dimensional Frequency-Encoding Partial Fourier Acquisition

Example 10. $T_2$*-Weighted Brain Imaging

Figure 12:
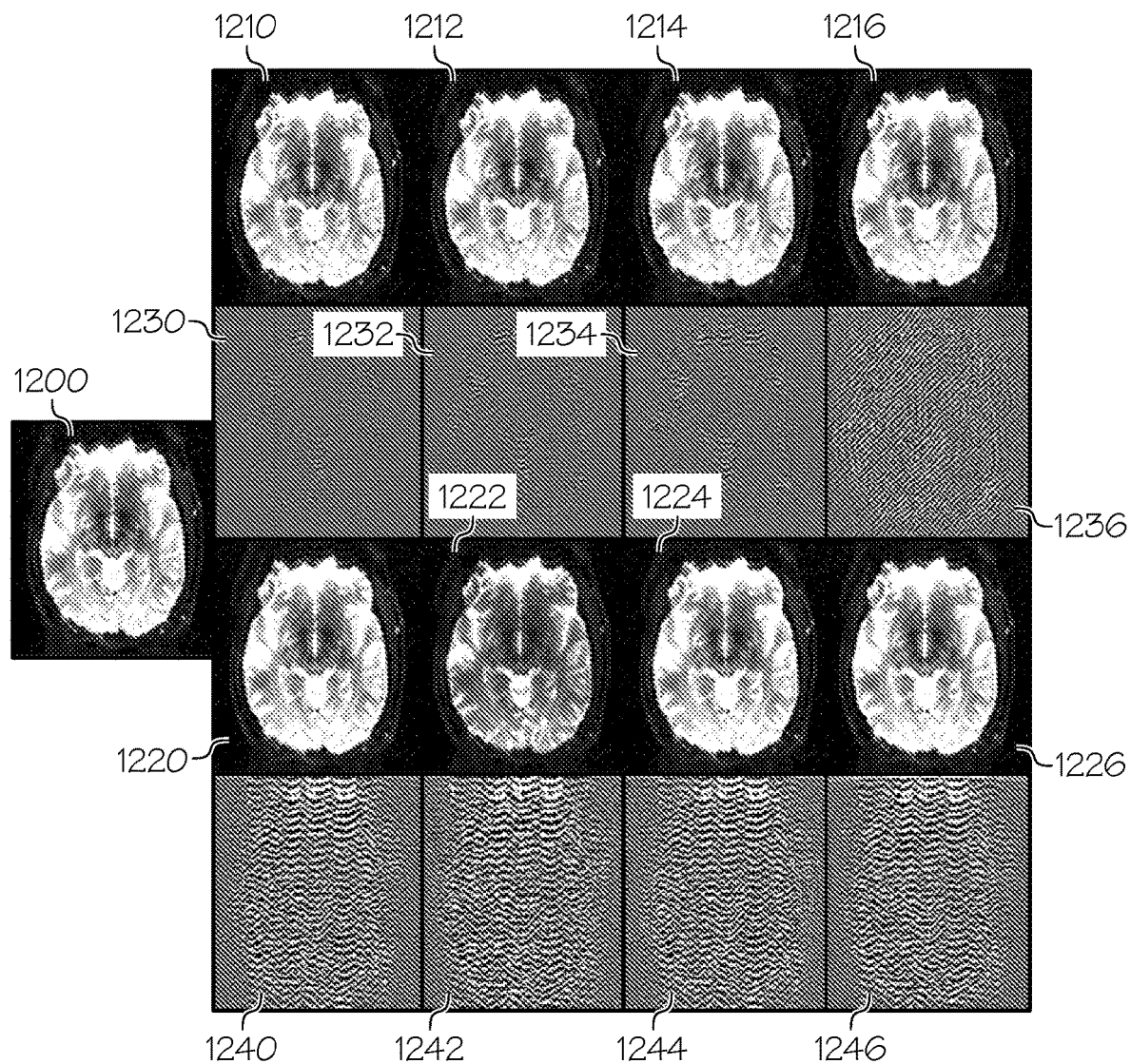
FIG. 12 shows an example of brain images of a healthy subject acquired with $T_2$*-weighted echo planar spin echo imaging sequence and their difference between the reconstructed images from full and partial k-space data at one phase encoding direction and one frequency encoding direction.

A $T_2$*-weighted brain image of a healthy subject is acquired by spin-echo echo planar imaging (EPI) sequence with FOV 240×240 mm², matrix 132×160, slice thickness 4 mm, TR 8100 ms, and TE 73 ms. FIG. 12 shows brain images reconstructed by the present method and zero-filling and their difference between the reconstructed images from full k-space data and partial k-space data with one dimensional phase-encoding and one dimensional frequency-encoding. All images reconstructed by the present method have a better quality over those reconstructed by zero-filling at the corresponding k-space coverage. An image 1200 reconstructed by full k-space is used as a reference. The partial Fourier acquisition was formed by removing a part of full k-space data.

The images 1210, 1212, 1214, 1216 are reconstructed from partial k-space dataset according to the present method. The image 1210 is reconstructed from partial k-space dataset at the k-space coverage of 62.5%. The image 1212 is reconstructed from partial k-space dataset at the k-space coverage of 55%. The image 1214 is reconstructed from partial k-space dataset at the k-space coverage of 47%. The image 1216 is reconstructed from partial k-space dataset at the k-space coverage of 39%. The images 1220, 1222, 1224, 1226 are reconstructed from partial k-space dataset using zero-filling. Images 1230, 1232, 1234, 1236 show difference between the image 1200 and the images 1210, 1212, 1214, 1216, respectively. Images 1240, 1242, 1244, 1246 show difference between the image 1200 and the images 1220, 1222, 1224, 1226, respectively.

Two dimensional phase encoding partial Fourier acquisition are performed at one dimensional phase encoding k-space coverage of 62.5% and other frequency-encoding k-space coverage of 100%, 87.5%, 75% and 62.5%, respectively. That is, total partial k-space coverage of 62.5%, 55%, 47% and 39%, respectively. The images 1210, 1212, 1214, 1216 reconstructed by the present method are clearer and sharper that the images 1220, 1222, 1224, 1226 reconstructed by zero-filling at the corresponding k-space coverage. Quantitative analysis indicated the RMSEs of the images 1210, 1212, 1214, 1216 relative to the image 1200 reconstructed from the fully sampled k-space data using the present method are much lower the RMSEs of the images 1220, 1222, 1224, 1226 obtained using zero-filling method as shown in Table 3 below.

TABLE 3

| K-space coverage | RMSE | | | | | | | |
|---|---|---|---|---|---|---|---|---|
| | 62.5% | | 55% | | 47% | | 39% | |
| Sequence | Zero-filling | Present method | Zero-filling | Present method | Zero-filling | Present method | Zero-filling | Present method |
| DWI (b = 0) | 0.075 | 0.002 | 0.075 | 0.0037 | 0.075 | 0.0065 | 0.075 | 0.042 |
| DWI (b = 1000) | 0.036 | 0.0034 | 0.037 | 0.012 | 0.038 | 0.011 | 0.056 | 0.0243 |

The RMSEs of the images 1210, 1212, 1214, 1216 are 0.2%, 0.37%, 0.65% and 4.2% at the k-space coverage of 62.5%, 55%, 47% and 39%, respectively. The RMSEs of the images 1220, 1222, 1224, 1226 are all around 7.5% for the zero-filling method. Thus, the present method provides more accurate images than zero filling based partial Fourier reconstruction method in the $T_2$-weighted brain imaging.

Example 11. Diffusion-Weighted Brain Imaging

Figure 13:
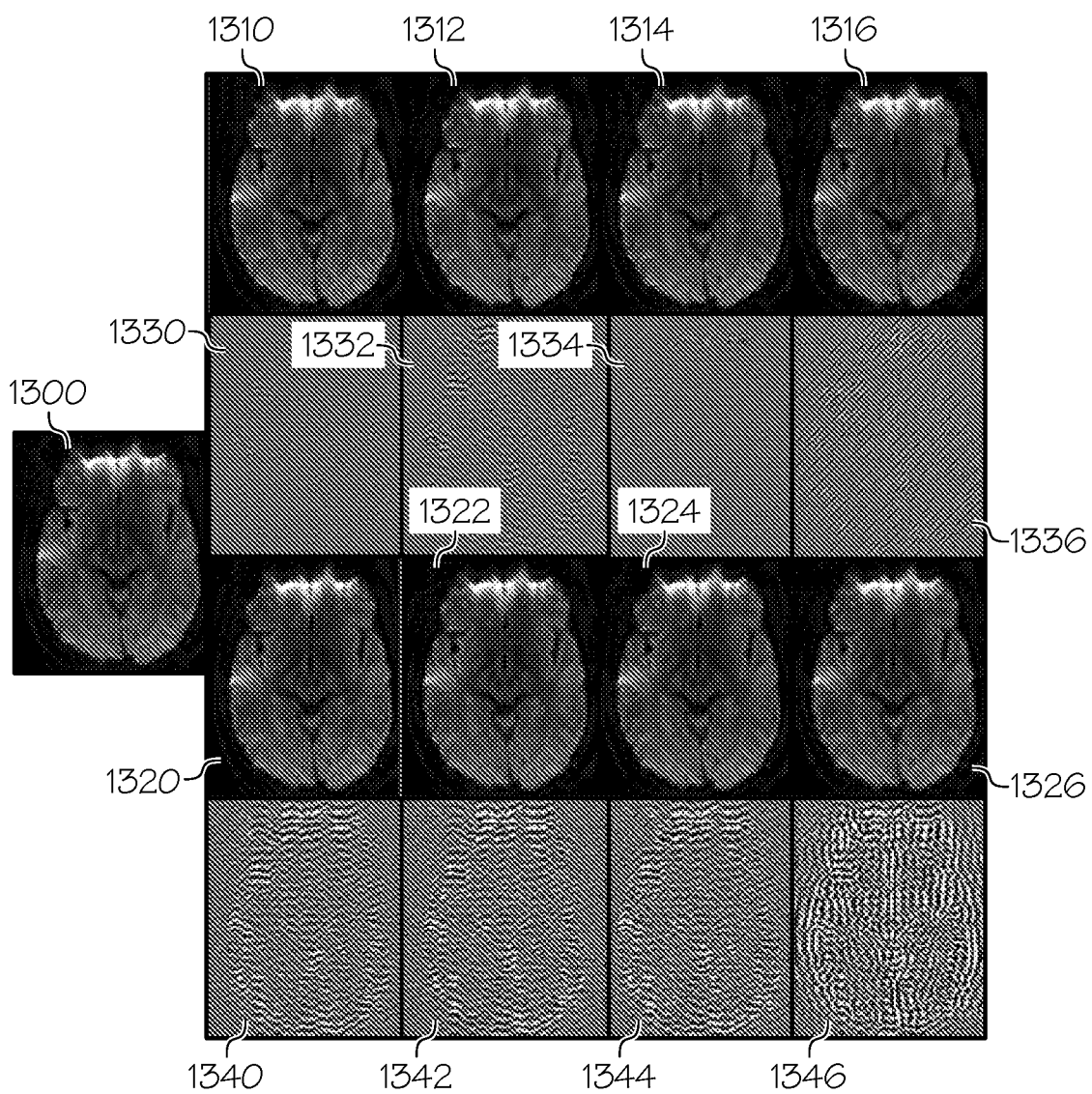
FIG. 13 shows an example of brain images of a healthy subject acquired with diffusion-weighted sequence at b=1000 s/mm$^2$ and their difference between the reconstructed images from full and partial k-space data at one phase encoding direction and one frequency encoding direction.

A diffusion-weighted brain image is acquired by spin-echo echo planar imaging sequence with FOV 240×240 mm², matrix 132×160, slice thickness 4 mm, TR 8100 ms, TE 73 ms, and b value=1000 s/mm². FIG. 13 shows brain images reconstructed by the present method and zero-filling and their difference between the reconstructed images from full k-space data and partial k-space data with one dimensional phase-encoding and one dimensional frequency-encoding. All images reconstructed by the present method have a better quality over those reconstructed by zero-filling at the corresponding k-space coverage. The image 1300 reconstructed by full k-space is used as a reference. The partial Fourier acquisition was formed by removing a part of full k-space data.

The image 1300 reconstructed by full k-space is used as a reference. The images 1310, 1312, 1314, 1316 are reconstructed from partial k-space dataset according to the present method. The image 1310 is reconstructed from partial k-space dataset at the k-space coverage of 62.5%. The image 1312 is reconstructed from partial k-space dataset at the k-space coverage of 55%. The image 1314 is reconstructed from partial k-space dataset at the k-space coverage of 47%.

The image 1316 is reconstructed from partial k-space dataset at the k-space coverage of 39%. The images 1320, 1322, 1324, 1326 are reconstructed from partial k-space dataset using zero-filling. Images 1330, 1332, 1334, 1336 show difference between the image 1300 and the images 1310, 1312, 1314, 1316, respectively. Images 1340, 1342, 1344, 1346 show difference between the image 1300 and the images 1320, 1322, 1324, 1326, respectively.

Two dimensional phase encoding partial Fourier acquisition are performed at one dimensional phase encoding k-space coverage of 62.5% and other frequency-encoding k-space coverage of 100%, 87.5%, 75% and 62.5%, respectively. That is, total partial k-space coverage of 62.5%, 55%, 47% and 39%, respectively. The images 1310, 1312, 1314, 1316 reconstructed by the present method are clearer and sharper that the images 1320, 1322, 1324, 1326 reconstructed by zero-filling at the corresponding k-space coverage. Quantitative analysis indicated the RMSEs of the images 1310, 1312, 1314, 1316 relative to the image 1300 reconstructed from the fully sampled k-space data using the present method are much lower than the RMSEs of the images 1320, 1322, 1324, 1326 obtained using zero-filling method as shown in Table 3. The RMSEs of the images 1310, 1312, 1314, 1316 are 0.34%, 1.2%, 1.1% and 2.4% at the k-space coverage of 62.5%, 55%, 47% and 39%, respectively. The RMSEs of the images 1320, 1322, 1324, 1326 are 3.6%, 3.7%, 3.8% and 5.6% for the zero-filling method, respectively. Thus, the present method provides more accurate images than zero filling based partial Fourier reconstruction method in the diffusion-weighted brain imaging.

In summary, the reconstruction of images acquired with partial Fourier acquisition has been one of the oldest and the toughest MRI techniques. The objective of this disclosure demonstrates a general new method to reconstruct partial Fourier reconstruction images even when image phase changes rapidly. The present method may be performed by Hermitian symmetry and k-space data correction which correction transformation matrix is estimated using acquired central k-space of partial Fourier k-space dataset. The present method greatly outperforms zero-filling method which is widely used in commercially MRI scanners. The RMSE of the reconstructed brain images based on the present method is about from 89% to 97% smaller than that of the reconstructed brain images based on zero-filling method at the different k-space coverage and image acquisition sequences. The present method is not insensitive to sequence type, rapid phase changes and long echo time. Therefore, the present method may replace zero-filling method for partial Fourier image reconstruction in clinical and research practices.

In the present disclosure, un-acquired k-space data is corrected using identical dimension transformation matrix which is directly estimated by the low-resolution data in k-space domain. The present method greatly outperforms zero-filling method for partial Fourier reconstruction of the brain images acquired with $T_1$-weighted, $T_2$-weighted and diffusion-weighted sequences.

The present method provides several technical advantages. First, the synthesized k-space data and their correction are conducted in k-space domain, while conventional partial Fourier reconstruction methods (such as standard homodyne reconstruction) conducted the synthesized k-space data and their correction in image domain. The conventional methods approximately estimate phase information in image space using low-resolution image which is reconstructed from the center of acquired k-space. The conventional methods using low-resolution images introduce truncation artifacts and compromise the image resolution. Additionally, zero-filling method compromises the image resolution and may cause Gibbs ringing.

Second, the present method avoids the reconstruction error caused from reduced dimension date. For 2 dimensional (2D) image with phase encoding partial Fourier acquisition, conventional partial Fourier reconstruction ignores the phase variation along frequency encoding and estimates phase variation along the phase encoding. Though there is no partial Fourier acquisition along frequency encoding direction, various factors, such as $B_0$ inhomogeneity and susceptibility difference, can introduce 3 dimensional (3D) phase changes that influence k-space data along phase encoding and frequency encoding directions. These factors influence phase changes along both phase encoding and frequency encoding directions. One dimensional phase information estimated by conventional partial Fourier reconstruction cannot describe the phase variation of un-acquired high-frequency data exactly. As a result, the reconstructed images by the phase information and Hermitian symmetry introduce artifacts. Similarly, reduced dimension phase information estimated by conventional partial Fourier reconstruction methods result in error in the phase changes of un-acquired high-frequency data exactly for 3D image with two phase encoding and/or frequency encoding partial Fourier acquisition.

Third, conventional partial Fourier reconstruction is very sensitive to the sequence type. Generally, conventional Fourier reconstruction works better for spin echo based sequence than gradient echo sequence because Hermitian symmetry in k-space is normally perfectly satisfied for a spin-echo sequence but not for $T_2^*$-weighted sequence (e.g. gradient echo sequence and echo planar imaging sequence). The present method is insensitive to the sequence type. The performance for $T_2^*$-weighted spin echo EPI sequence—in FIG. 7 is even slightly better than that for $T_2$-weighted FSE sequence in FIG. 5. The result suggests that the present method may be very promising in $T_2^*$-weighted sequence at high field strength because it produce small error for correcting synthesized un-acquired k-space data from Hermitian symmetry.

Fourth, conventional partial Fourier reconstruction methods work well only for imaging acquisitions that allow a very short TE. The shorter TE can reduce the effect of chemical shift and $B_0$ inhomogeneity on the related phase, and lead to reduced motion-related phase. These method may be problematic for long TE because $T_2^*$ effect is not negligible and the assumption of Hermitian symmetry introduce a error in partial Fourier reconstruction, particularly for a $T_2^*$-weighted sequence. In FIGS. 7 and 5, the present method works well at TE of 100 ms for fast spin echo sequence and 73 ms for spin echo EPI sequence, respectively. There is little difference in RMSEs of reconstructed images. The difference in RMSE may result from the different signal-to-noise ratio for the two images. The result suggests that the present method is not sensitive to long TE. Such features make the present method more attractive for diffusion weighted imaging and functional MRI at ultra-high field strength when the $T_2^*$ relaxation become shorter.

Finally, partial Fourier acquisition is widely used in EPI acquisition to reduce the TE and thereby improve the signal-to-noise ratio. However, conventional partial Fourier reconstruction methods fail to treat correctly the rapid phase variation across the tissue and introduce the oscillatory artifacts across the image. For example, partial Fourier acquisition increases the sensitivity of EPI sequence to bulk motion and shifts the points or lines in k-space. If the points and lines are displaced into the high-frequency k-space data, conventional partial Fourier reconstruction method may cause intensity oscillations across the image and increase RMSE. The present method avoids this problem by estimating k-space displacement in k-space and reconstruct high quality brain images, as shown in FIGS. 7 and 8. That is, the present method work well in rapid phase changes of the images acquired with EPI sequences. In this study, we only discuss EPI sequence with the partial Fourier acquisition in phase encoding direction. Generally, the partial Fourier reconstruction of phase encoding is more accurate than that of frequency-encoding because TE generally is less than TR. The phase changes caused by $B_0$ inhomogeneity and chemical shift are proportional to the time. That is, shorter duration time of the k-space point acquisition will introduce the smaller phase changes.

In summary, the present partial Fourier reconstruction may be performed by Hermitian symmetry and k-space data correction which correction matrix is estimated using acquired central k-space of partial Fourier k-space dataset. In vivo brain imaging experiments indicate that the present method outperforms zero-filling method for partial Fourier image reconstruction. The present method is not insensitive to sequence type, rapid phase changes and long TE. Furthermore, the present method is compatible with various fast imaging techniques, such as parallel imaging acquisition and compressed sensing.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

The invention claimed is:

1. A method for medical image registration in k-space domain, the method comprising:
   receiving, using a controller, a first partial k-space dataset for an object and a second partial k-space dataset for the object;
   selecting, using the controller, the first partial k-space dataset as a reference;
   selecting, using the controller, feature for estimating a transformation matrix for transforming k-space data;
   estimating, using the controller, a transformation matrix based on the feature of entire or part of the first partial k-space dataset and the feature of the second partial k-space dataset corresponding to the entire or part of the first partial k-space dataset;
   correcting, using the controller, the second partial k-space dataset based on the transformation matrix;
   obtaining, using the controller, the corrected second partial k-space dataset; and
   storing the corrected second partial k-space dataset in an image data storage unit for magnetic resonance reconstruction.

2. A method for Magnetic Resonance Imaging (MRI) partial Fourier reconstruction, the method comprising:
   acquiring, using a controller, a first partial k-space dataset for a target area using an MRI scanner;
   creating, using the controller, a second partial k-space dataset for the target area based on Hermitian symmetry of the first partial k-space dataset;
   calculating, using the controller, a transformation matrix based on the first partial k-space dataset and the second partial k-space dataset;
   correcting, using the controller, the second partial k-space dataset using the transformation matrix;
   obtaining, using the controller, a full k-space dataset for the target area based on at least one of the corrected second partial k-space dataset, the first partial k-space dataset, and a third k-space dataset;
   constructing, using the controller, an image for the target area based on the full k-space dataset; and
   storing the corrected second partial k-space dataset in an image data storage unit for magnetic resonance reconstruction.

3. A magnetic resonance imaging (MRI) system comprising:
   a magnetic field generating unit configured to apply a plurality of RF pulses with a variable flip angle to a target area in an object;
   a receiver configured to receive MR signals from the target area;
   a processing unit;
   a system memory; and
   machine readable instructions stored in the system memory that, when executed by the processing unit, cause the processing unit to:
      acquire a first partial k-space dataset for the target area based on the MR signals;
      create a second partial k-space dataset for the target area based on Hermitian symmetry of the first partial k-space dataset;
      calculate a transformation matrix based on the first partial k-space dataset and the second partial k-space dataset;
      correct the second partial k-space dataset using the transformation matrix;
      obtain a full k-space dataset for the target area based on at least one of the corrected second partial k-space dataset, the first partial k-space dataset, and a third k-space dataset;
      reconstruct an image for the target area based on the full k-space dataset; and
      output the image through an output device.

4. The method of claim 1, wherein receiving the first partial k-space dataset and the second partial k-space dataset comprises:
   acquiring the first partial k-space dataset and the second partial k-space dataset from at least one modality; or
   determining the first partial k-space dataset and the second partial k-space dataset from corresponding images of electronic storage on image domain; or
   determining the first partial k-space dataset and the second partial k-space dataset from a mathematic model.

5. The method of claim 1, wherein the feature includes at least one of a phase of k-space data that object feature is mainly weighted by image magnitude of a magnetic resonance image associated with the k-space domain, or a magnitude of k-space data that object feature is mainly weighted by image phase of the magnetic resonance image associated with the k-space domain.

6. The method of claim 5, wherein the feature comprises at least one of a phase of k-space data that are acquired with $T_1$-weighted or its variation sequence, or a magnitude of k-space data that are acquired with $T_2$-weighted, $T_2^*$-weighted, or their variation sequence.

7. The method of claim 1, wherein the transformation matrix is configured to transform the first partial k-space dataset or the second partial k-space dataset by at least one of translation, rotation, scaling and shearing of the first partial k-space dataset, or the second partial k-space dataset.

8. The method of claim 4, wherein the at least one modality is at least one of optical image, CT, MRI, ultrasound, and PET.

9. The method of claim 2, wherein the first partial k-space dataset is a partial Fourier k-space dataset; and wherein the partial Fourier k-space dataset is acquired in at least one of phase-encoding and frequency-encoding direction.

10. The method of claim 2, wherein calculating the transformation matrix comprises:

estimating the transformation matrix based on a part of the first partial k-space dataset and a corresponding part of the second partial k-space dataset.

11. The method of claim 2, wherein calculating the transformation matrix comprises:

acquiring a full Fourier k-space dataset for the target area using an MR scanner with a resolution that is lower than a resolution used for acquiring the first partial k-space dataset; and calculating the transformation matrix based on the full Fourier k-space dataset and the second partial k-space dataset.

12. The method of claim 11, wherein the transformation matrix is configured to correct translation, rotation, scaling and shearing of an entire or part of k-space dataset.

13. The method of claim 2, wherein the third k-space dataset comprises a k-space dataset which is not covered by the first k-space dataset and the second k-space dataset.

14. The method of claim 13, wherein the third k-space dataset is filled with zeros, or the third k-space dataset extends a boundary of the first k-space dataset or the second k-space dataset.

15. The method of claim 2, wherein the full k-space dataset is filtered using at least one of hard thresholding, Hamming filtering, Hanning filtering, Blackman filtering, Lanczos filtering, Gaussian filtering, and Wiener filtering.

16. The method of claim 2, wherein the first partial k-space dataset is acquired using at least one of rectilinear, echo planar, a propeller, a blade, radial, Cartesian, non-Cartesian, Zig-Zag, stochastic, rosette, TWIRL, WHIRL and spiral trajectories.

17. The method of claim 2, wherein the first partial k-space dataset is acquired using at least one of a sequential sampling order, a centric sampling order, an interleave sampling order, a reverse sampling order, a random sampling order, or a hybrid sampling order.

18. The method of claim 2, wherein acquiring the first partial k-space dataset for the target area using the MRI scanner comprises controlling the MRI scanner to acquire the first partial k-space dataset with a fraction of less than 0.8.

19. The method of claim 2, wherein acquiring the first partial k-space dataset for the target area using the MRI scanner comprises controlling the MRI scanner to acquire the first partial k-space dataset with a fraction of less than 0.6.

20. The method of claim 2, wherein acquiring the first partial k-space dataset for the target area using the MRI scanner comprises controlling the MRI scanner to acquire the first partial k-space dataset with a fraction of less than 0.4.

* * * * *